US006291439B1

(12) United States Patent
Klock

(10) Patent No.: US 6,291,439 B1
(45) Date of Patent: Sep. 18, 2001

(54) METHODS FOR DIAGNOSING ATHEROSCLEROSIS BY MEASURING ENDOGENOUS HEPARIN AND METHODS FOR TREATING ATHEROSCLEROSIS USING HEPARIN

(75) Inventor: John C. Klock, Nicasio, CA (US)

(73) Assignee: BioMarin Pharmaceuticals, Novato, CA (US)

( * ) Notice: Subject to any disclaimer, the term of this patent is extended or adjusted under 35 U.S.C. 154(b) by 0 days.

(21) Appl. No.: 09/145,477

(22) Filed: Sep. 2, 1998

(51) Int. Cl.$^7$ .................. G01N 27/26; G01N 27/447
(52) U.S. Cl. .................. 514/56; 204/452; 204/603
(58) Field of Search .................. 514/56; 536/21; 204/452, 461, 603, 612

(56) References Cited

U.S. PATENT DOCUMENTS

| | | | |
|---|---|---|---|
| 4,852,137 | 7/1989 | Mackay | 378/62 |
| 4,874,492 | 10/1989 | Mackay | 204/461 |
| 4,975,165 | 12/1990 | Brandley | 204/461 |
| 5,035,786 | 7/1991 | Brandley et al. | 204/461 |
| 5,087,337 | 2/1992 | Brandley et al. | 204/461 |
| 5,094,731 | 3/1992 | Brandley et al. | 204/461 |
| 5,094,740 | 3/1992 | Brandley et al. | 204/464 |
| 5,205,917 | 4/1993 | Klock, Jr. | 204/461 X |
| 5,316,638 | 5/1994 | Jackson | 204/464 |
| 5,340,453 | 8/1994 | Jackson | 204/461 |
| 5,472,582 | 12/1995 | Jackson | 204/459 |

FOREIGN PATENT DOCUMENTS

WO 93/10450 * 5/1993 (WO).

OTHER PUBLICATIONS

P. Oreste et al, "Micromethod for Determination of Heparin in Plasma after Intravenous and Subcutaneous Administration" Analytical Biochemistry, vol. 210, pp. 136–139, 1993.*

Simone Cavari et al, "Detection of Heparin–like Glycosaminoglycans in Normal Human Plasma by Polyacrylamide–gel Electrophoresis" Clinica Chimica Acta, vol. 252, pp. 159–170, 1996.*

R. Erik Edens et al, "Two–Dimensional Affinity Resolution Electro–phoresis Demonstrates that Three Distict Heparin Populations Interact with Antithrombin III", Biochemistry, vol. 34, No. 8, pp. 2400–2407, 1995.*

Reinhard Malsch et al, "Chromatographic and Electrophoretic Applications for the Analysis of Heparin and Dermatan Sulfate" Journal of Chromatography B, vol. 685, pp. 223–231, 1996.*

Christopher M. Starr et al, "Fluorophore–assisted Carbohydrate Electrophoresis in the Separation, Analysis, and Sequencing of Carbohydrates", Journal of Chromatography A, vol. 170 pp. 295–321, 1996.*

Christopher M. Starr, "Flurophore–assisted Electrophorasis of Urinary Carbohydrates for the Identification of Patients with oligo–saccharidosis–and mucopolysaccharidosis–type Lysosomal Storage Diseases," Glycosylation & Disease, vol. 1 No. 3, pp. 165–176, 1994.*

John C. Klock et al, "The Different Faces of Disease, FACE Diagnosis of Disease" Glycoimmunology, Edited by A. Alavi and d.S. Axford pp. 13–25, 1995.*

Hyman Engelberg, "Evidence that Endogenous Heparin Activity Deficiency may be an Important Factor in Atherogenis," Seminars in Thrombosis and Hemostatis, vol. 23, No. 2 pp. 159–166, 1997.*

Agatston, et al., "Quantification of Coronary Artery Calcium Using Ultrafast Computed Tomography," *J. American Coll. Cardio.*, 159(4):827–832 (1990) No Month Available.

Arad, et al., "Predictive Value of Electron Beam Computed Tomography of the Coronary Arteries: 19–Month Follow–up of 1173 Asymptomatic Subjects," *Circulation*, 93:1951–1953 (1996) No Month Available.

Baker, et al., "Inability of the Activated Partial Thromboplastin Time to Predict Heparin Levels," *Arch. Intern. Med.*, 157:2475–2479 (1997) No Month Available.

Biological Abstract, Phiadelphia, PA USA; Abstract No. PREV199799667135 (1997) No Month Available.

Bjornsson, et al., "Heparin kinetics determined by three assay methods," *Clin. Parmacol. Ther.*, 31(1):104–113 (1982) No Month Available.

Broze, et al., "Regulation of Coagulaion by a Multivalent Kunitz–Type Inhibitor," *Biochemistry* 29(33):7539–7546 (1990) No Month Available.

Cadroy, et al., "Delayed Elimination of Enoxaparine in Patients with Chronic Renal Insufficiency," Thromb. Res. 63:385–390 (1991) No Month Available.

Casu, "Structure of Heparin and Heparin Fragments," *Heparin and Related Polysaccharides, Structure and Activities*, Ofusu and Hirsh eds. Ann NY Acad. Sci., 556:1–17 (1989) No Month Available.

Cavari, et al., "Endogenous Heparinase–Sensivite Anticoagulant Activity in Human Plasma," *Thromb. Res.*, 67:157–165 (1992) No Month Available.

(List continued on next page.)

*Primary Examiner*—Jill Warden
*Assistant Examiner*—John S. Starsiak, Jr.
(74) *Attorney, Agent, or Firm*—Albert P. Halluin; Luisa Bigornia; Howrey Simon Arnold & White, LLP

(57) ABSTRACT

The present invention provides methods for measuring endogenous heparin in a mammal at levels that were previously undetectable. The present invention further features methods for assessing the risk for and assessing the progression of atherosclerosis and methods for treating or inhibiting the progression of atherosclerosis. The invention also features methods for monitoring plasma heparin levels in subjects undergoing heparin treatment. Additionally, the present invention provides kits for assaying for heparin in biological samples.

14 Claims, 12 Drawing Sheets

OTHER PUBLICATIONS

Ceustermans, et al., "Preparation, Characterization, and Turnover Properties of Heparin–Antithrombin III Complexes Stablized by Covalent Bonds," *J. Biol. Chem.*, 257(7):3401–3408 (1982) No Month Available.

Chen and Yang, Versatile, Non–Cloting–Based Heparin Asssay Requiring No Instrumentation, *Clin. Chem.*, 37(6):832–837 (1991) No Month Available.

de Stuart, et al., Kinetics of Intravenously Administered Heparin in Normal Humans, *Blood*, 60(6):1251–1258 (1982) No Month Available.

Durrington, "How HDL protects against atheroma," *Lancet* 342:1315–1316 (1993) No Month Available.

Engleberg, "Endogenous Heparin Activity Deficiency and Atherosclerosis," *Clin. Appl. Thromb/Hemostasis.*, 2(2):83–93 (1996) No Month Available.

Engelberg, "Plasma Heparin Levels, Correlation with Serum Cholesterol and Low –Density Lipoproteins," *Circulation* 23:573–577 (1961) No Month Available.

Engelberg, "Evidence That Endogenous Heparin Activity Deficiency may be an Important Factor in Atherogenesis," *Seminars in Thrombosis and Hemostasis*, 23(2):159–166 (1997) No Month Available.

Engelberg, "Update on the Relationship of Heparin to Atherosclerosis and Its Thrombotic Complications," *Sem. Thromb. Hemo.*, 14:88–105 (1988) No Month Available.

Fareed, et al., "Modulation of Endothelium by Heparin and Related Polyelectrolytes," Clin. Appl. Thrombosis/Hemostasis, 2(3):200–208 (1996) No Month Available.

Guo, and Conrad, "Analysis of Oligosaccharides from Heparin by Reversed–Phase Ion–Pairing High–Performance Liquid Chromatogoraph," *Anal. Biochem.*, 168:54–62 (1988) No Month Available.

Hirsch, et al., "Heparin Kenetics in Venous Thrombosis and Pulmonary Embolism," *Circulation*, 53(4):691–696 (1976) No Month Available.

Hirsh and Fuster, "Guide to Anticoagulant Therapy Part 1: Heparin," *Circulation*, 89(3):1449–1468 (1994) No Month Available.

Hirsch, "Heparin," *New England J. Med.*, 324(22):1565–1574 (1991) No Month Available.

Hyers, et al., "Antithrombotic Therapy for Venous Thromboembolic Disease," *Chest*, 108(4):335S–351S (1995) No Month Available.

Honda, et al., "Analysis of the Oligosaccharides in Oval-Bumin By High–performance Capillary Electrophoresis," *Anal. Biochem*, 191:228–234 (1990) No Month Available.

Jackson, J. "The use of polyacrylamide–gel electrophoresis for the high–resolution separation of reducting saccharides labelled with the fluorophor 8–aminonaphthalene–1,3,6, –trisulphonic acid," *Biochem*, 270:705–713 (1990) No Month Available.

Kayser, "Heparin: Mechanism of Action", Textbook of Therapeutics: Drug and Disease management Herfindal and Gourley eds., 861 (1996) No Month Available.

Klock and Starr, "The Different Faces of Disease, Face Diagnosis of Disease," *Glycoimmunology* Alavi and Axford eds., 13–25 (1995) No Month Available.

Vachvanichsanong, et al., Internat. Pediatr. 9:40–48 (1994) No Month Available.

Klock, et al. Pharmacokinetics by direct biochemical measurement of heparin and low molecular weight heperin using Face, First Internet Glycotechnology Conference (Sep., 1995) No Month Available.

Kristensen, et al., "Effect of Tissue Factor Pathway Inhibitor (TFPI in the HEPTEST® Assay and in an Amidolytic Anti Factor Xa Assay for LMW Heparin," *Thromb. Haemost.*, 68(3):310–314 (1992) No Month Available.

Levine, et al. "A Randomized Trial Comparing Activated Thromboplastin Time With Heparin Assay in Patients With Acute Venous Thromboembolism Requiring Large Daily Doses of Heparin," *Arch. Intern. Med.*, 154:49–56 (1994) No Month Available.

Lindahl, et al., "Extrinsic Pathway Inhibitor (EPI) Released to the Blood by Heparin is a More Powerful Coagulation Inhibitor Than is Recombinant EPI," *Thromb. Res.*, 62:607–614 (1991) No Month Available.

Liu, et al., "Separation of Fluorescent oligosaccharide derivatives by microcolumn techniques based on electrophoresis and liquid chromatorgraphy," *J. Chromatography*, 559:223–235 (1991) No Month Available.

Ma, et al., "Electrochemical Sensor for Heparin: Further Characterization and bioanalytical Applications," *Anal. Chem.*, 65:2078–2084 (1993) No Month Available.

Manson, et al., "The variable anticiagulant response to unfractionated heparin in vivo reflects binding to plasma proteins rather than clearance," *J. Lab Clin. Med.* 130:649–655 (1997) No Month Available.

Majerus, et al., "Anticoagulant Thrombolytic, and Antiplatelet Drugs," *The Pharmacological Basis of Therapeutics 9th ed.*, McGraw–Hill eds., pp. 1341–1359 No Date Available.

McAvoy, "The biologic half–life of heparin," *Clin. Pharmacol. Thera.*, 25(3):372–379 (1979).

Mesters, et al., "Markers of coagulation activation for evaluation of the antithrombotic efficacy of heparin: a prospective sutdy in acute deep venous thrombosis," *Blood Coague Fibrinolysis*, 6:665–671 (1995) No Month Available.

Metcalfe, "Mastocytosis", *Cecil Textbook of Medicine 18th ed.*, Wyngaarden et al., ed., pp 1493–1495 (1988) No Month Available.

Nyman, et al., "Heparin Dosage in Extracorporeal Circulation and Its Neutralization," *Thrombos. Diathes. Haemorrh.*, 33:102–104 (1974) No Month Available.

Oreste, et al., "Micromethod for the Determination of Heparin in Plasma after Intravenous and Subcutaneous Administration," *Anal. Biochem.*, 210:136–139 (1993) No Month Available.

Rapaport, "The Extrinsic Pathway Inhibitor: A Regulator of Tissue Factor–Dependent Blood Coagulation," *Thromb. Haemost.*, 66(1):6–15 (1991) No Month Available.

Rappaport and Rao, "The Tissue Factor Pathway: How It Has Become a 'Prima Ballerina'," *Thromb. Haemost.*, 74(1):7–17 (1995) No Month Available.

Shojania, et al., "The Variations Between Heparin Sensitivity of Different Lots of Activated Partial Thromboplastin Time Reagent Produced by the Same Manufacturer," *Am. J. Clin. Pathal.*, 89:19–23 (1988) No Month Available.

Silvestro, et al., "Human Pharmacokinetics of Glycosaminoglycans Using Deuterium–labeled and Unlabeled Substances: Evidence for Oral Absorption," *Sem. Thromb. Hem.*, 20(3):281–292 (1994) No Month Available.

Simon, et al., "Extracoronary Atherosclerotic Plaque at Multiple Sites and Total Coronary Calcification Deposit in Asymptomatic Men, Association With Coronary Risk Profile," *Circulation*, 92(6):1414–1421 (1995) No Month Available.

Singh, et al., "Enantiomers of HA–966 (3–amino–1–hydroxypyrrolid–2–one) exhibit distinct central nervous system effects: (+)–HA–966 is a selective glycine/N–methyl–D–asparate receptor antagonist, but (−)–HA–966 is a potent γ–butyrolactone–like sedative," *Proc. Natl. Acad. Sci.*, 87:347–351 (1990) No Month Available.

Starr, et al., "Fluorophore–assisted electrophoresis of urinary carbohydrates for the identification of patients with oligosaccharidosis– and mucopolysaccharidosis–type lysosomal storage diseases," *Glycosylation & Disease*, 1(3):165–176 (1994).

Starr, et al., "Fluorophore–assisted carbohydrate electrophoresis in the separation, analysis, and sequencing of carbohydrates," *J. Chromatography*, 720:295–321 (1996) No Month Available.

Torri, et al., "Nuclear Magnetic Resonance Analysis of Human Urine: Influence of Intravenous and Oral Administration of Glycosaminoglycans," *Sem. Thromb. Hem.*, 20(2):144–151 (1994) No Month Available.

van den Besselaar, et al., "Monitoring Heparin Therapy: Relationships between the Activated Partial Thromboplastin Time and Heparin Assays Based on Ex–Vivo Heparin Samples," *Thromb. Haemost.*, 63:(1):16–23 (1990) No Month Available.

Wessler and Gitel, "Heparin: New Concepts Relevant to Clinical Use," *Blood*, 53(4):525–544 (1979) No Month Available.

\* cited by examiner

IS HEPARIN DISACCHARIDE LEVEL IN A NORMAL PATIENT (1391)

IS HEPARIN DISACCHARIDE LEVEL IN A PATIENT WITH ATHEROSCLEROSIS (850)
CHANNEL A: FLUORESCENCE

FIG. 5

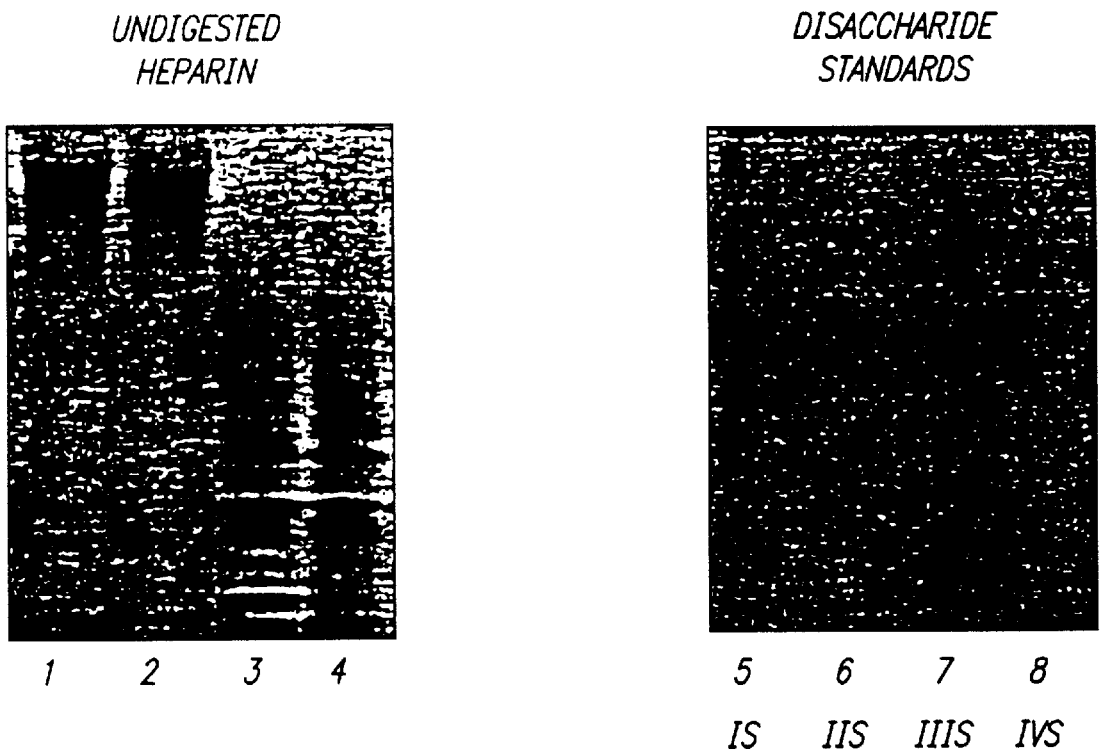

PROFILING AND DISACCHARIDE
ANALYSIS OF HEPARIN

UNDIGESTED HEPARIN — lanes 1 2 3 4

DISACCHARIDE STANDARDS — lanes 5 6 7 8
IS   IIS   IIIS   IVS

LANE 1 BOVINE LUNG HEPARIN
LANE 2 PARTIAL DIGEST OF HEPARIN WITH HEPARINASE
LANE 3 FURTHER HEPARINASE DIGEST
LANE 4 COMPLETE HEPARINASE DIGEST
LANE 5 $\alpha\Delta UA2S$ (1-4) GLcNS6S DISACCHARIDE (IS)
LANE 6 $\alpha\Delta UA$ (1-4) GLcNS6S DISACCHARIDE (IIS)
LANE 7 $\alpha\Delta UA2S$ (1-4) GLcNS DISACCHARIDE (IIIS)
LANE 8 $\alpha\Delta UA$ (1-4) GLcNS DISACCHARIDE (IVS)

METHODS FOR DIAGNOSING ATHEROSCLEROSIS BY MEASURING ENDOGENOUS HEPARIN AND METHODS FOR TREATING ATHEROSCLEROSIS USING HEPARIN

FIELD OF THE INVENTION

The present invention is in the field of medicine and biochemistry, particularly heparin chemistry. In particular, the invention provides a novel method for diagnosing atherosclerosis and predicting the risk for developing atherosclerosis by measuring the amount of endogenous heparin present in a mammal. The invention also provides novel methods for measuring levels of endogenous heparin in a mammal and methods for treating atherosclerosis by administering heparin to individuals identified according to the methods of the invention.

BACKGROUND OF THE INVENTION

Carbohydrates play a number of important roles in the functioning of living organisms. In addition to their metabolic roles, carbohydrates are structural components of the human body covalently attached to numerous other entities such as proteins and lipids (called glycoconjugates). For example, the human endothelium cell surface makeup includes a glycoprotein matrix. The carbohydrate portion of this matrix imparts important properties to the endothelial cell surface and internal blood vessel structure as well as affecting the fluidity of the blood which interacts with the endothelium surface.

Atherosclerosis is a disease characterized by changes in the endothelium and the underlying stromal compartment with cellular proliferation and accumulation of lipid-filled macrophages. This disease kills over a million Americans every year (American Heart Association, 1998, *Heart and Stroke Statistical Update*). The numbers of people affected but asymptomatic is probably higher due to the lack of early diagnostic techniques. Early in the disease process, clinical symptoms are absent and the disease is usually not recognized by the patient or physician. By the time clinical symptoms manifest, a significant amount of morbidity and mortality have occurred.

Preventive techniques to control the onset of atherosclerosis include physical activity, a healthy diet, cessation of smoking and weight loss (US Preventative Services Task Force, *Guide to the Clinical Preventative Services*, $2^{nd}$ ed., Baltimore, Williams & Wilkins, 1996). These intervention therapies require accurate and sensitive measures of atherosclerosis to be able to adequately assess immediate and long-term efficacy. One of the best measures of susceptibility to atherosclerosis is assessment of coronary artery calcium (Arad et al., *Circulation* 93:1951–1953 (1996); Simon et al., *American Heart Association* 92:1414–1421 (1995)). Although assessing levels of coronary artery calcium yields measurements that have been shown to be highly correlated with risk factors, these measurements do not provide information on the chance for a thrombotic event. It is clear that more accurate and sensitive methods for early detection of coronary atherosclerosis and risk for coronary thrombosis are needed.

A number of biochemical measurements in the blood are associated with an increased risk of developing atherosclerosis. These include glucose, lipids, lipoproteins, apolipoproteins and homocystine. In assessing these new tests, it is important to establish that they can, in practice, be used to predict development of the actual condition of atherosclerosis rather than a "risk-factor" for the tendency to develop atherosclerosis. The validation of predictive factors is urgent due to the need to apply emerging new treatments for atherosclerosis to those individuals at high risk.

Some have speculated that endogenous heparin levels are inversely related to cholesterol and lipoprotein levels (Engelberg, *Circulation* 23:573–577 (1961)). However, an effective way to measure endogenous heparin and correlate the levels present with atherosclerotic risk have not been available previously.

Glycosaminoglycans are sugar chains consisting of repeating polymers of acidic polysaccharides. These materials are composed of building blocks of the following sugars in various combinations: galactose, glucose, N-acetylglucosamine, N-acetylgalactosamine, glucuronic acid, galacturonic acid and iduronic acid. In addition these sugar units may be variably linked α or β at their anomeric carbons and (1–3) or (1–4) to their ring carbons through an O-glycosidic bond. Finally they may be variably substituted with sulfates at their 2,3,4 or 6 carbons. Depending on the precise repeating disaccharide structure and location of sulfates, human connective tissue glycosaminoglycans are commonly classified as chondroitin sulfates, dermatan sulfates, heparan sulfates, heparin sulfates and keratan sulfates (Collins, *Carbohydrates*, London, Chapman Hall, (1987)). Glycosaminoglycans are carbohydrates that are integrally associated with the endothelium and are thought to be the major source of naturally-occurring anticoagulants in human blood.

Glycosaminoglycans (GAGs) are present in mammalian blood, urine and other body fluids and are sensitive markers for the diagnosis of lysosomal storage diseases (Klock et al., *Internat Pediatr*, 9:40–48 (1994); Starr et al., *Glycosylation & Disease* 15 1:165–176 (1994)). Degradation products of GAGs are found in urine. The concentration of individual carbohydrates in a sample can be measured by FACE®, an acronym standing for the technique of fluorophore—assisted carbohydrate electrophoresis. The FACE technique is described in detail in U.S. Pat. Nos. 4,975,165, 5,035,786, 5,087,337, 5,094,731, 5,094,740, 5,205,917, 5,316,638, 5,340,453, and 5,472,582, the disclosures of which are herein incorporated by reference. FACE® permits the electrophoretic separation of a complex mixture of carbohydrates into distinct bands on a gel. Prior to electrophoresis, a carbohydrate mixture for analysis is treated with a charged fluorescent tag that combines with the reducing end of the carbohydrates for analysis. The fluorescent label permits the quantitative measurement of the labeled carbohydrates. The charged tag not only fluorescently labels the carbohydrates, but imparts an ionic charge, thus permitting hitherto uncharged carbohydrates to migrate in an electric field. Suitable fluorescent labels include 8-aminonapthalene -1,3, 6-trisulphonic acid (ANTS), 1-amino-4-napthalene sulfonic acid (ANSA), 1-amino-6,8-disulphonic acid (ANDA),2-aminoacridone and lucifer yellow. After the carbohydrates have been labeled, the sample is subjected to polyacrylamide gel electrophoresis in order to separate and concentrate the labeled carbohydrates into bands. The separated carbohydrates may be visualized directly by fluorescence under ultraviolet light. Alternatively the separated carbohydrates may be visualized by means of a laser-scanner photomultiplier tube system, a charge coupled device (CCD). CCD's are semiconductor imaging devices that permit the sensitive detection of emitted light.

CCD's and their uses are described in U.S. Pat. No. 4,874,492, the disclosure of which is herein incorporated by reference. The image produced by the CCD may be subsequently transferred to a computer wherein the bands may be analyzed with respect to intensity, mobility, standards, and the like.

The development of FACE® technology (Jackson, *Biochem J* 270:705–713 (1990)) and its adaptation for measuring carbohydrate analytes in several disease processes (Klock et al., "The Different Faces of Disease, FACE Diagnosis of Disease", *Glycoimmunology*, eds. Alavi and Axford, (1995) pages. 13–25) have provided a new method for high-resolution separation of nanomolar quantities of monosaccharides and oligosaccharides derived from human tissues. The separation of carbohydrates using CE has been described in recent publications, such as Honda et al., *Biochem*. 191:228–234 (1990) and Liu et al., *J. Chromatography*, 559:223–235 (1991). The present invention is based in part on the discovery that the increased sensitivity of the FACE® heparin assay now makes it possible to measure endogenous production of heparin in the blood and urine. The present invention also takes advantage of the increased sensitivity of the FACE® heparin assay to provide novel methods for monitoring heparin levels in patients receiving heparin treatment and to provide novel methods for diagnosing, assessing risk for and treating atherosclerosis.

There was greater than 90% correlation between the calcium score and the endogenous heparin level in these patients. One normal patient showed absence of coronary artery calcium and undetectable endogenous heparin.

Figure 4:
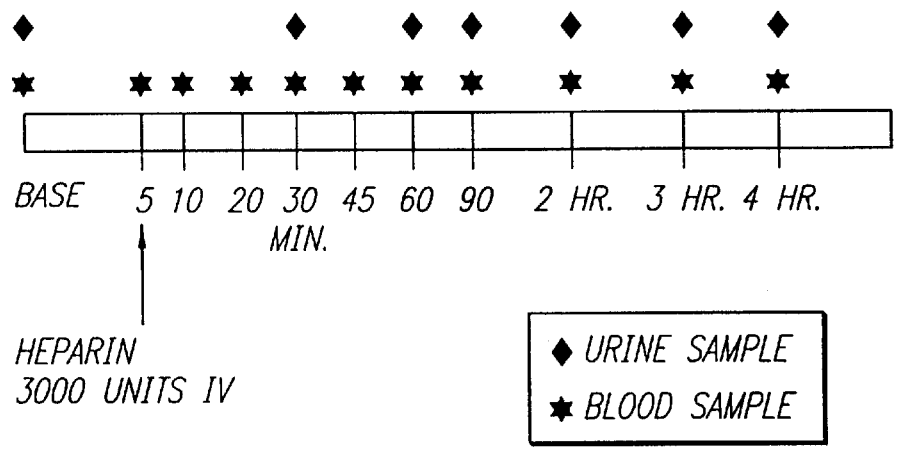

FIG. 4 represents the schedule of urine samples before and after intravenous infusion of 3000 units of unfractionated heparin in four male and one female volunteers. Urine samples were obtained at baseline, prior to infusion of heparin, and at 30, 60, 90, 120, 180 and 240 minutes in subjects 3, 4 and 5, and at baseline and 60 minutes in subjects 1 and 2.

FIG. 5 represents the FACE® analysis of bovine lung heparin. The left panel shows FACE® analysis of bovine lung heparin before and after heparinase digestion. The right panel shows FACE® analysis of standard heparin disaccharides.

Lane 1 is a ladder of glucose polymers G1 to G16. Lane 2 is IS an IVS heparin disaccharides. Lane 3 represents undigested heparin. Lane 4 represents an early heparinase digest. Lane 5 represents a late heparinase digest. Lane 6 represents a complete heparinase digest. Lane 7 represents $\alpha\Delta UA2S(-4)G1cNS6S$ (IS). Lane 8 represents $\alpha\Delta UA2S(1-4)G1cNS6S$ (IIS). Lane 9 represents $\alpha\Delta UA(1-4)G1cNS$ (IIIS). Lane 10 represents $\alpha\Delta UA(1-4)G1cNS$ (IVS).

Figure 6:
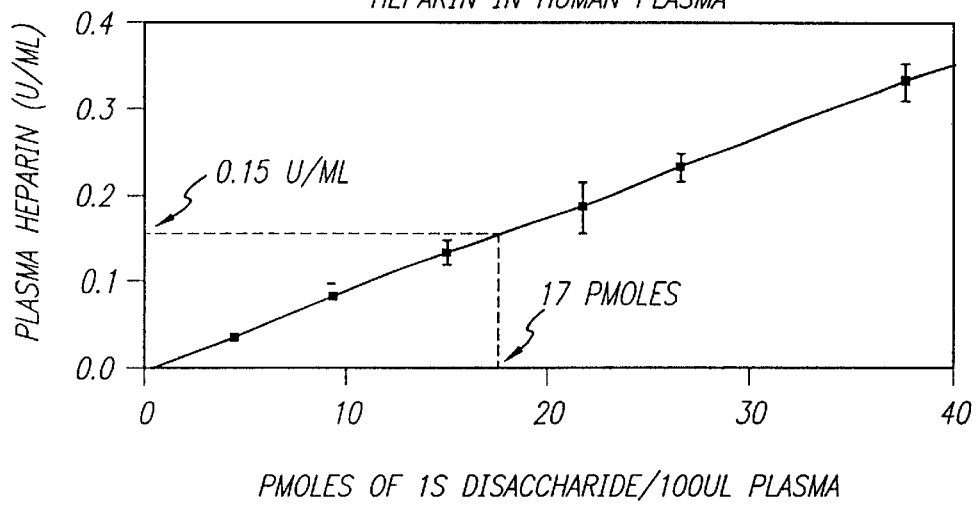

FIG. 6 represents the dynamic range of FACE® heparin assay in plasma. This figure demonstrates the sensitivity and linearity of the plasma heparin assay. Results were obtained by diluting beef heparin into normal plasma at known unit amounts. The measurement is linear from 0.025 to 1.0 U/ml.

Figure 7:
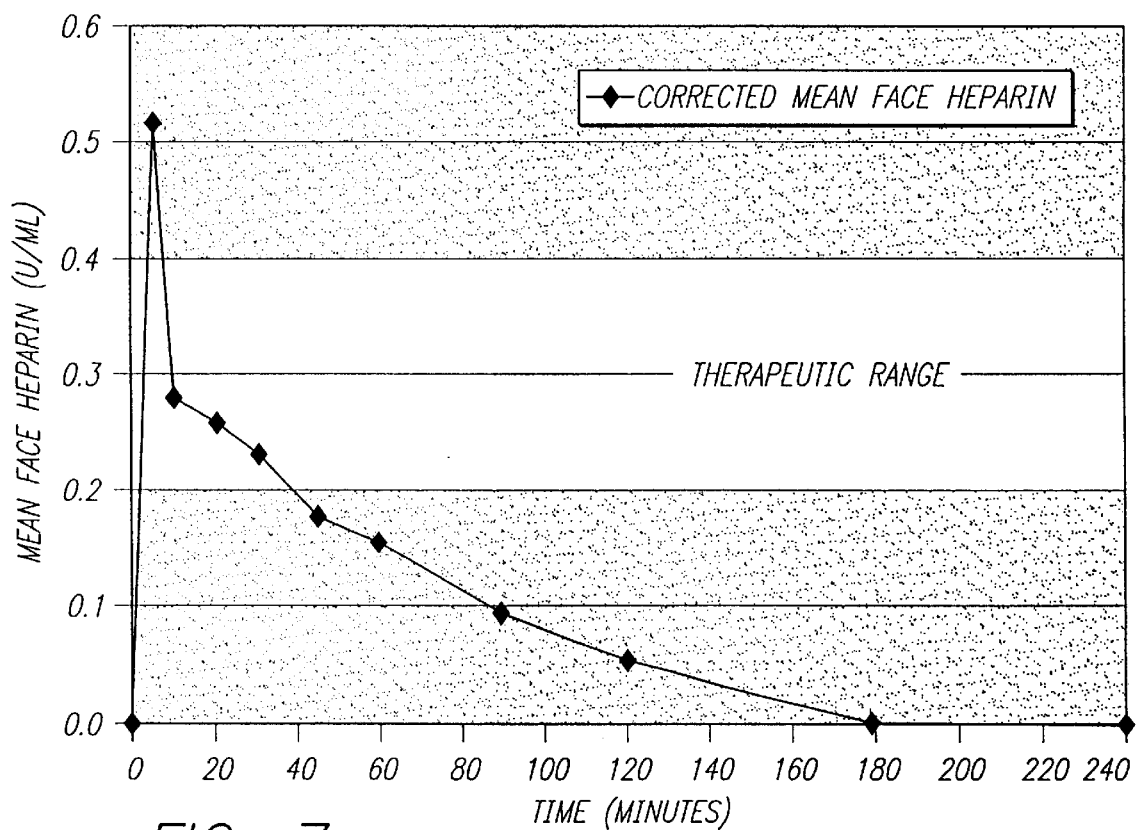

FIG. 7 represents direct measurement of FACE® heparin. Mean FACE® plasma heparin measurements are represented over a four hour period. Samples were obtained as outlined in FIG. 4. Mean values were obtained from seven subjects where each subject received a single 3,000 unit bolus of porcine heparin. Values were corrected for baseline values.

Figure 8:
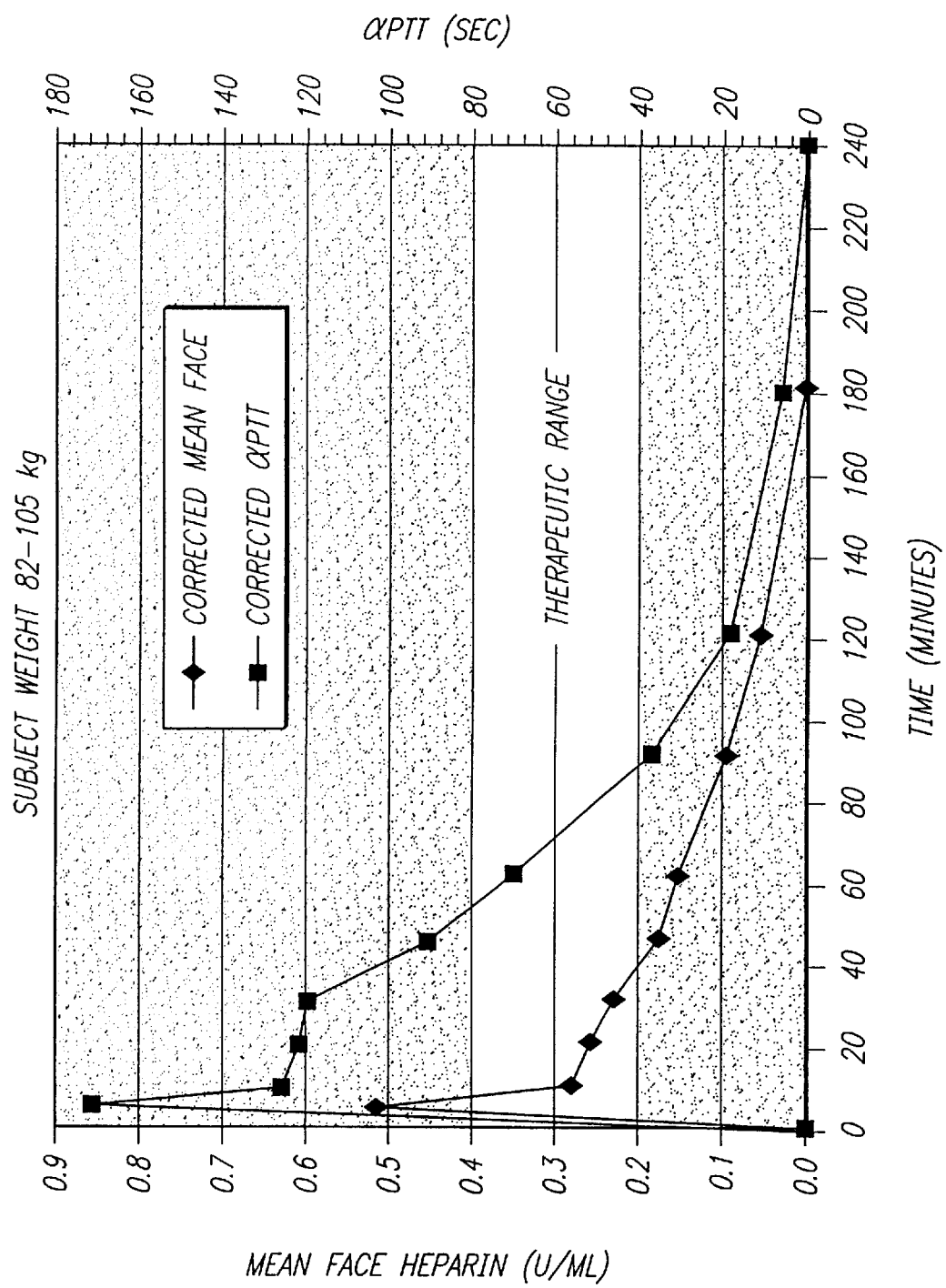

FIG. 8 represents FACE® heparin compared to $\alpha$PTT at high weight. The figure represents comparison of biochemcial heparin and $\alpha$PTT measurements in studies where subjects weighed between 82 and 105 kg. Values were corrected for baseline values.

Figure 9:
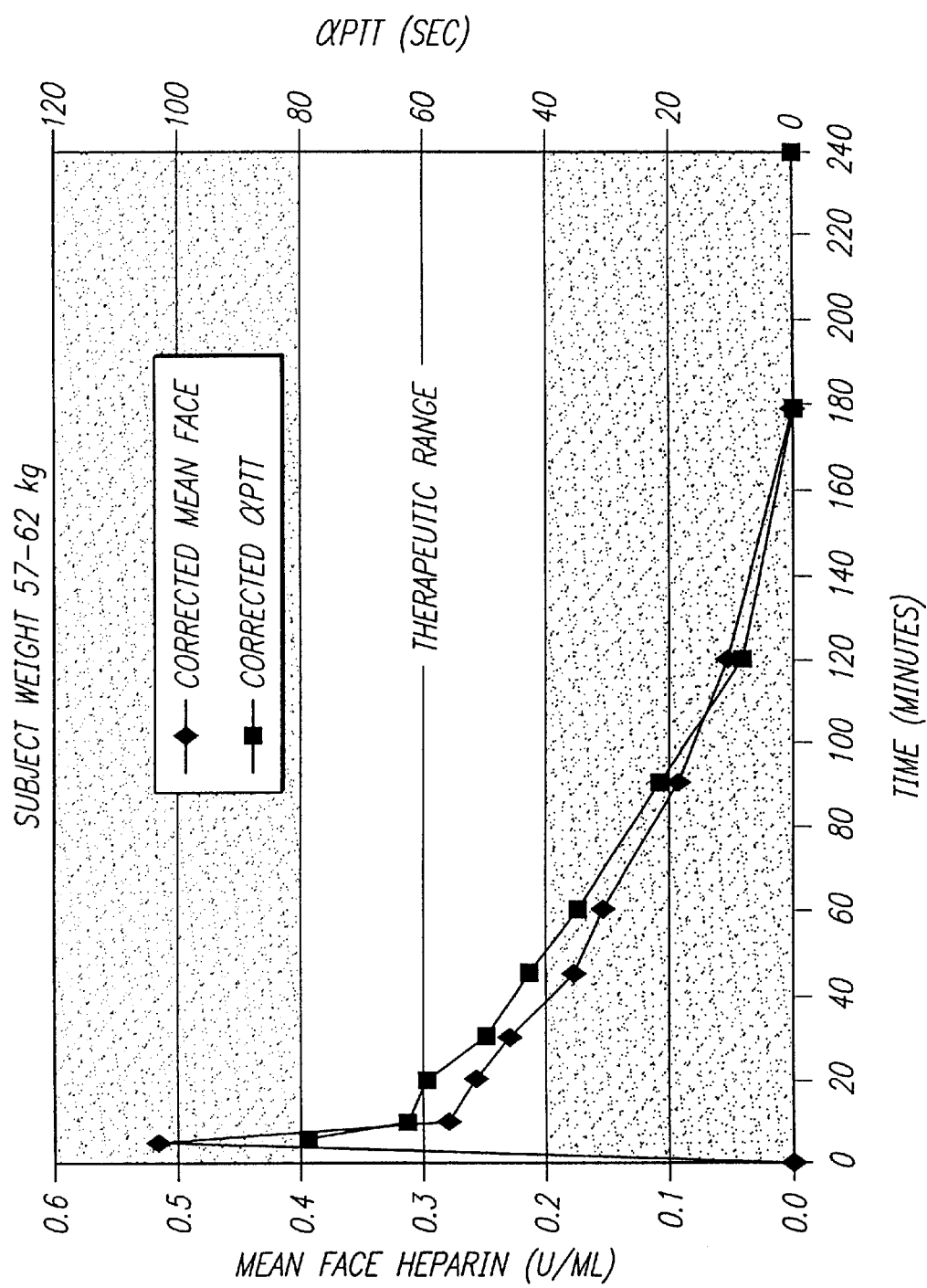

FIG. 9 represents FACE® heparin compared to $\alpha$PTT at low weight. The figure represents comparison of biochemcial heparin and $\alpha$PTT measurements in studies where subjects weighed between 57 and 62 kg. Values were corrected for baseline values.

Figure 10:
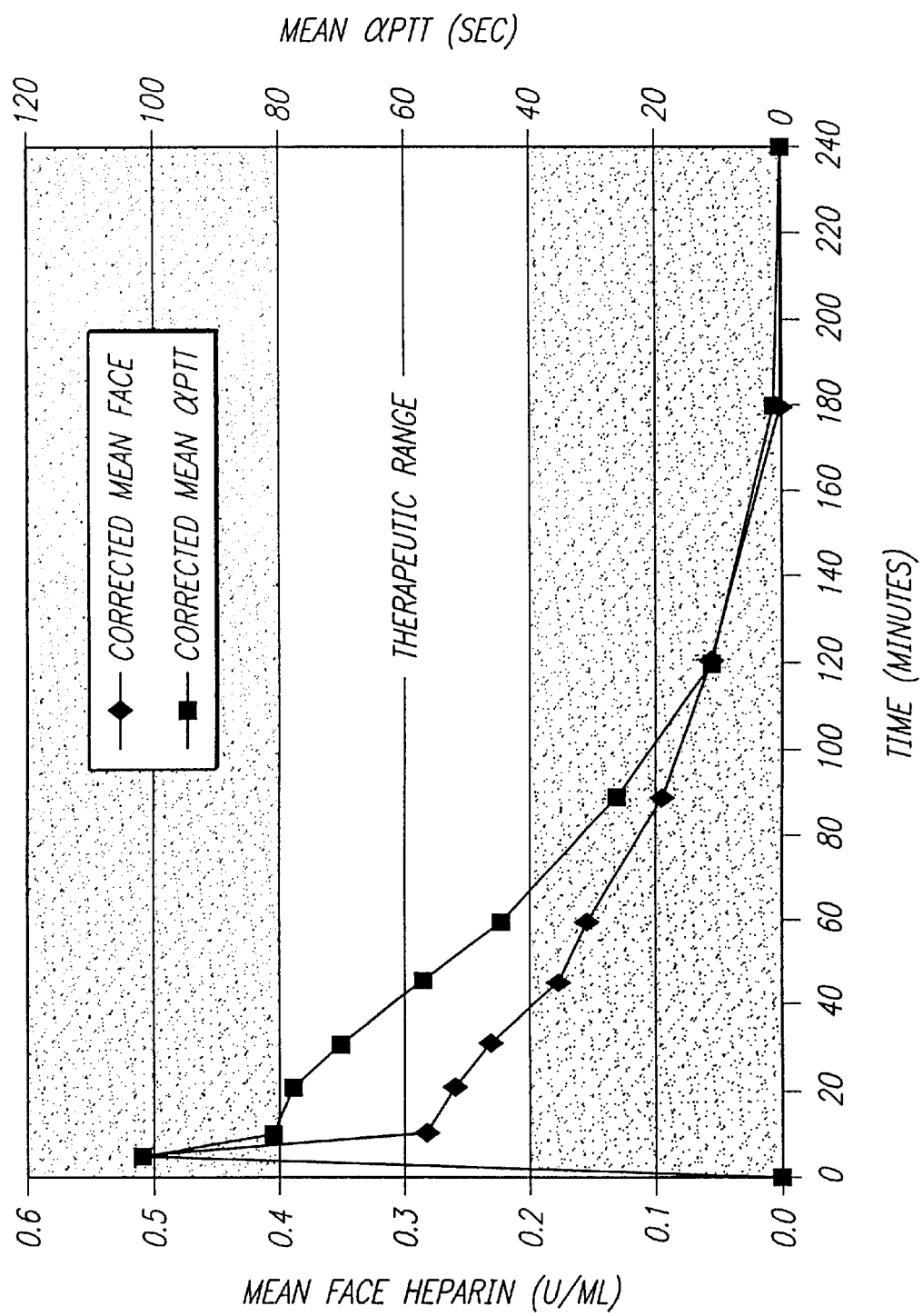

FIG. 10 represents a comparison of direct FACE® heparin to $\alpha$PTT. The figure represents biochemical heparin measurements and the PTT measured from the same sample at the same time points in seven subjects given 3,000 units of unfractionated heparin by intravenous bolus injection. Values were corrected for baseline values.

Figure 11:
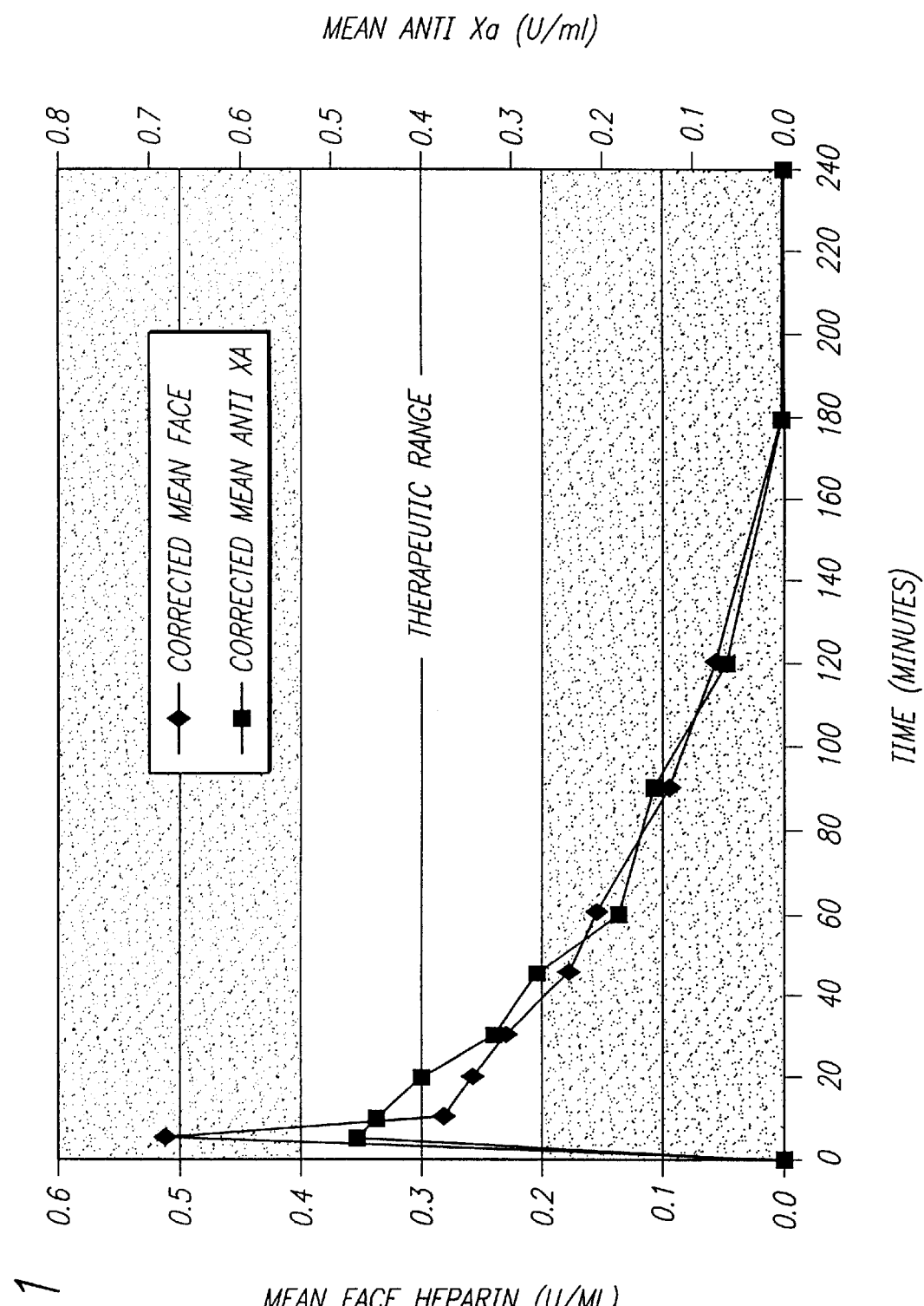

FIG. 11 represents a comparison of direct FACE® heparin to anti-Xa. The figure reports seven subject studies. Values were corrected for baseline values.

Figure 12:
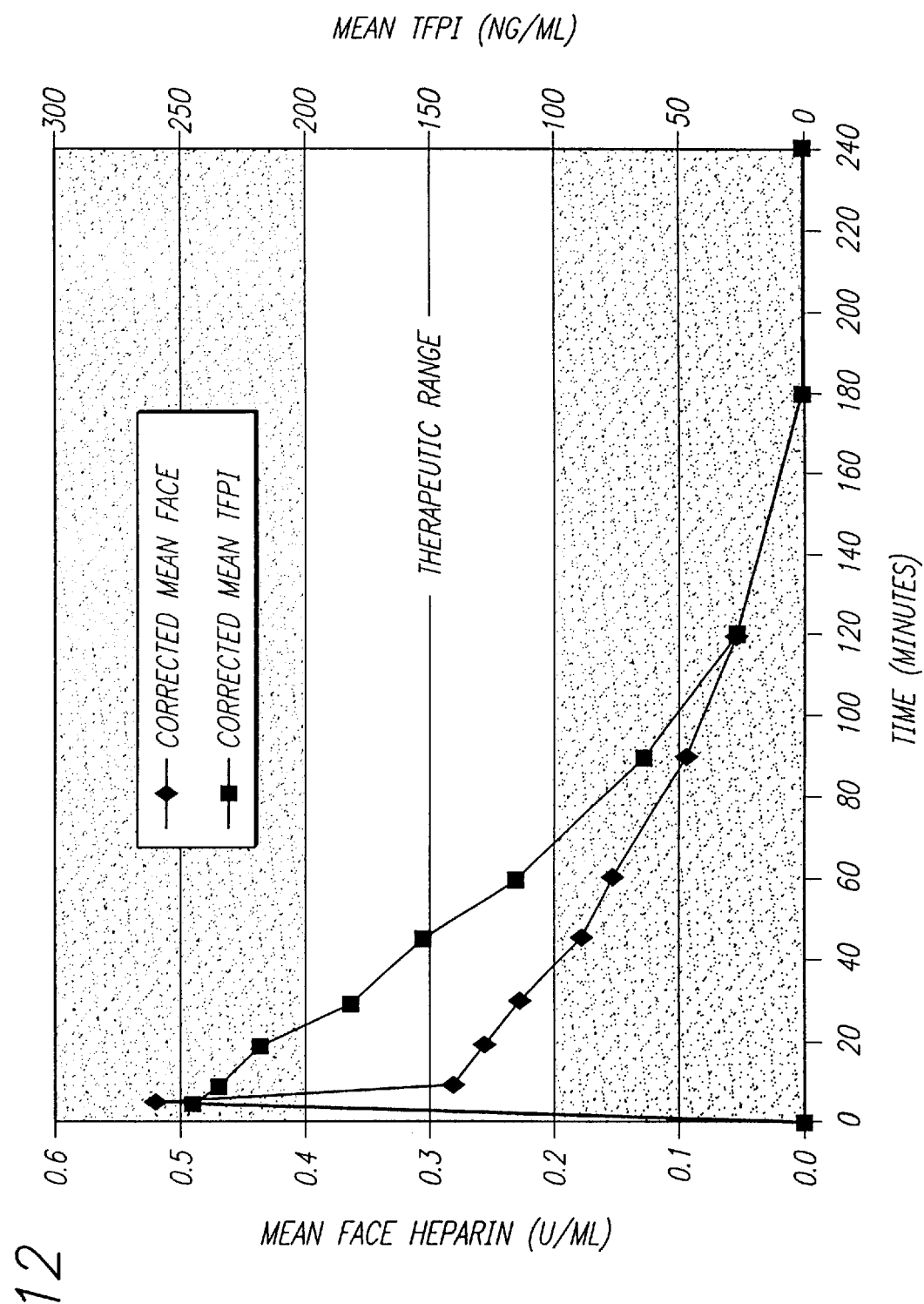

FIG. 12 represents a comparison of direct FACE® heparin assay and TFPI. The figure reports seven subject studies where each subject received a single 3,000 unit bolus of unfractionated heparin. Values were corrected for baseline values.

Figure 13:
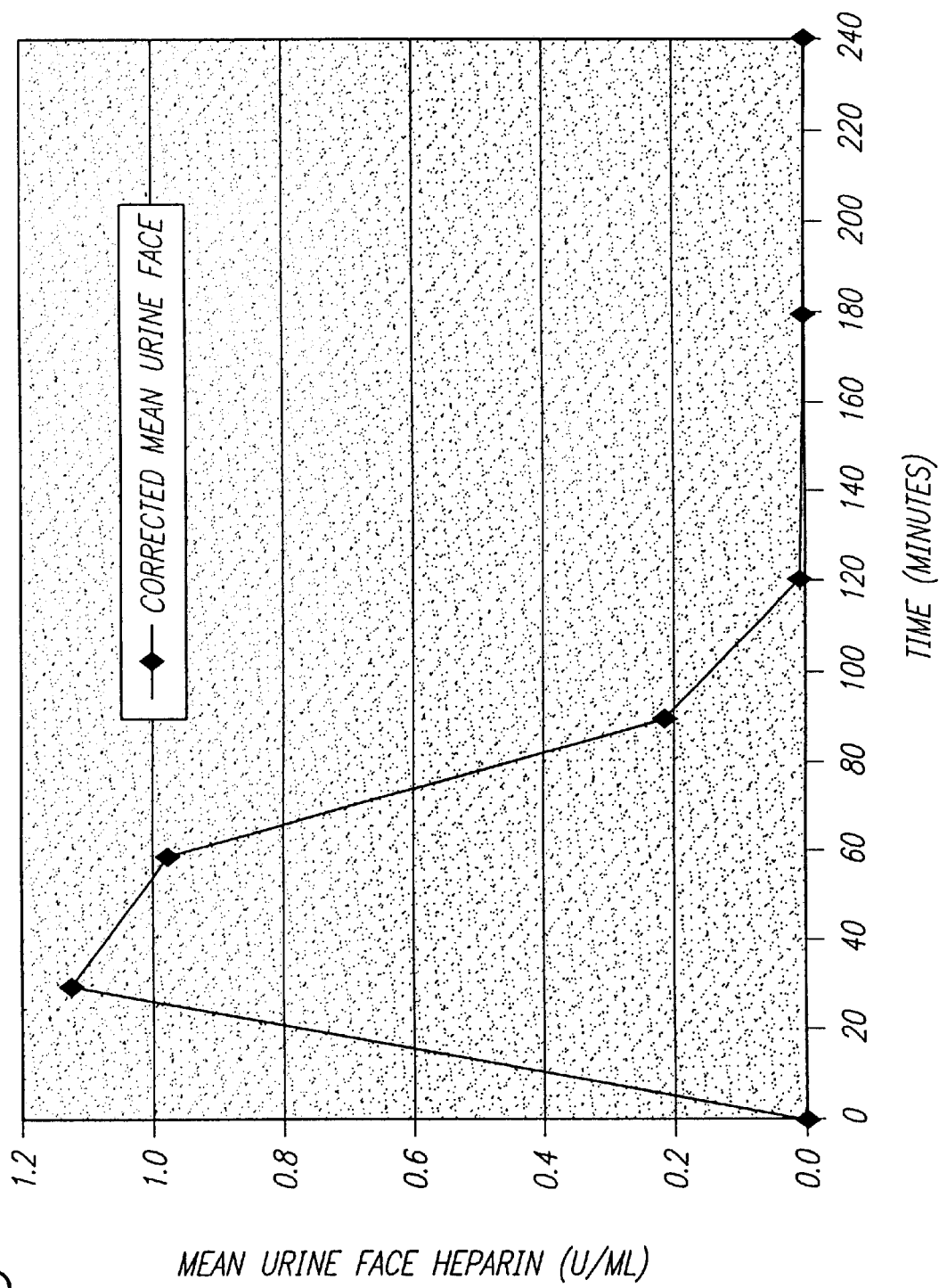

FIG. 13 demonstrates plasma and urine pharmacokinetics of unfractionated heparin in normal volunteers. These data demonstrate the mean and range of urine biochemical heparin levels that result from the infusion of 3,000 units of porcine heparin by intravenous bolus injection in seven subject studies. The urine heparin levels increased rapidly to peak at 30 minutes and returned to baseline by three hours. Time-volume calculations showed that the heparin recovered in urine was more than 80% of the amount injected.

Figure 14:
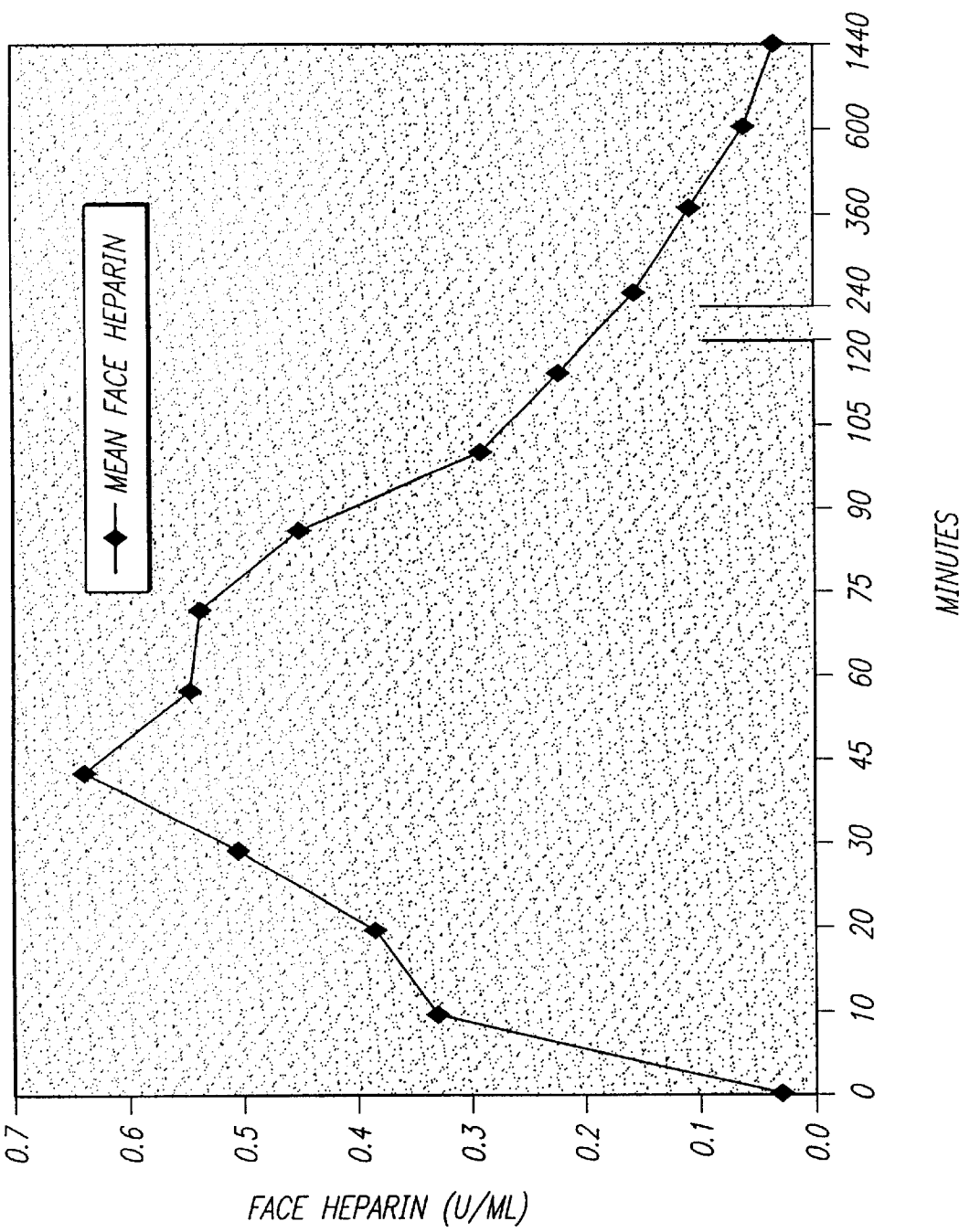

FIG. 14 represents direct heparin measurement of low molecular weight heparin. Mean heparin levels in two beagle dogs who received a subcutaneous injection of Enoxaprin (4 mg/kg) are presented. Samples were obtained over a 24 hour period. Peak elimination of heparin occurred at 45 minutes and reached baseline by 24 hours. The $T_{1/2}$ was approximately 135 minutes.

BRIEF SUMMARY OF THE INVENTION

In one aspect, the present invention features methods for measuring levels of endogenous heparin in a subject at levels that were previously undetectable. The present invention is based upon the discovery that particular diagnostic carbohydrates, specifically glycosaminoglycans (GAGs) such as heparin sulfate may be used to determine an imbalance between endogenous heparin production and formation of atherosclerotic plaques. The present invention is also based upon the discovery that a fluorophore-assisted carbohydrate electrophoretic process (FACE®) may be used to determine the presence of low levels of endogenously produced heparin.

In a second aspect, the present invention features methods for assessing risk for and monitoring the progress of development of atherosclerosis by determining the amount of endogenous heparin present in a mammal. In preferred embodiments of the invention, standards may be used to provide a comparison with the heparins in the subject samples. However, the information embodied by the standard, e.g, migration distance, mobility and intensity, may also be obtained from comparison with stored records made from standards previously subjected to analysis under similar conditions. Standards may be labeled prior to labeling the samples for analysis or standards may be labeled at the same time as the standards are labeled for analysis. Furthermore, the heparin in the standards is preferably quantified so as to provide for quantitative or qualitative comparisons with the amount of heparin in the samples for analysis. Individuals having heparin levels that are measured below the normal amounts may be assessed as at an increased risk for atherosclerosis. Risk values may be easily established for patient populations to correlate endogenous heparin levels with the risk for clinical atherosclerotic disease and sequelae resulting therefrom. Such sequelae include for example thrombotic events such as myocardial infarction and stroke. That is, endogenous heparin levels may be correlated to clinical events or clinical manifestations or measurements of atherosclerosis in a patient group.

In a third aspect, the present invention features methods for treating atherosclerosis and reducing the risk of clinical sequelae resulting from atherosclerosis comprising the step of administering heparin to a mammal. Individuals determined to have low levels of endogenous heparin according to the methods of the present invention may be treated by administering heparin in doses that are effective to prevent atherosclerosis or to inhibit the rate of progression of atherosclerosis. Such dosages may easily and routinely be determined by those skilled in the art.

In a fourth aspect, the present invention features a direct assay for monitoring plasma heparin levels. The FACE® heparin assay of the present invention can measure both unfractionated and low molecular weight heparin (LMWH) and allows measuring the efficacy of present and future anticoagulant treatment programs in a wide variety of conditions.

In a fifth aspect, the present invention features kits for assaying for the presence of heparins including heparin sulfate, analyzing biological samples for medical diagnosis, and for the synthesis or manufacture of heparins. Suitable kits enable laboratories to conveniently perform FACE®, FACE® analysis by capillary electrophoresis (FACE-CE), or some other method and may include reagents for performing tests to identify one or more specific results. Such kits may be useful for diagnosing atherosclerosis, assessing risk for developing atherosclerosis in a subject, or assessing severity of atheroslcerosis in a patient.

DETAILED DESCRIPTION OF THE INVENTION

In one aspect, the present invention features methods for measuring levels of endogenous heparin in a subject at levels that were previously undetectable. The present invention is based upon the discovery that particular diagnostic carbohydrates, specifically glycosaminoglycans (GAGs) such as heparin sulfate may be used to detect the presence of endogenously produced heparin and to determine an imbalance between endogenous heparin production and formation of atherosclerotic plaques.

The present invention is also based upon the discovery that a fluorophore-assisted carbohydrate electrophoretic process (FACE®)) may be used to determine the presence of low levels of endogenously produced heparin.

The present invention provides methods for detecting, measuring, testing and analyzing a heparin sulfate to determine the presence of and quantity of this substance in human body fluids. The invention further provides methods for identifying endogenous levels of heparin sulfate that cannot be detected by any prior art methods.

Heparin is a highly sulfated, long-chain polysaccharide of N-acetyl-glucosamine alternating with either glucuronic or iduronic acid with an average molecular weight in the unfractionated form in excess of 15,000 daltons (UFH). The average molecular weight of low molecular weight heparin (LMWH) is approximately one-third that of UFH. Heparin functions as an anticoagulant by binding to and modulating blood serine proteases and activated clotting factors, primarily through the heparin-antithrombin III (ATIII) complex. A unique pentasaccharide responsible for the binding of heparin to ATIII is found only on one-third of heparin molecules (Hirsch, *New Engl J Med* 324:1565 (1991)). Both forms of heparin are capable of releasing tissue factor pathway inhibitor (TFPI), a natural anticoagulant found in the endothelial cells lining the blood vessels (Fareed et al. *Clin Appl Thrombosis/Hemostasis* 2(3):200–208 (1996)). The primary use of heparin is to treat thrombotic disorders such as deep venous thrombosis. Although the individual response to heparin is variable, its efficacy relies on a dose of heparin that will prevent further clot formation. Inadequate initial treatment with heparin can lead to recurrent thromboembolic events. Heparin has other biologic activities, one of which may cause bleeding, a major complication of therapy. This complication is most often encountered when the dose of heparin is in excess of that required to prevent further clot formation.

Heparin sulfate is a common material found in all mammalian connective tissues. It is a variably N- and O-sulfated polymer of disaccharides of [-glucuronic acid $\beta(1-4\_-$N-acetylglucosamine-$\beta$ $(1-4)$-$]_n$; and [-iduronic acid $\alpha$ $(1-4)$-N-acetylglucosamine -$\beta$ $(1-4)$-$]_n$. (Casu, "Structure of Heparin and Heparin Fragments", in Heparin and Related Polysaccharides, Structure and Activities, Ofusu and Hirsh eds., *Ann N.Y. Acad Sci* 556:1–17 (1989)). These variations in sulfation are set forth below:

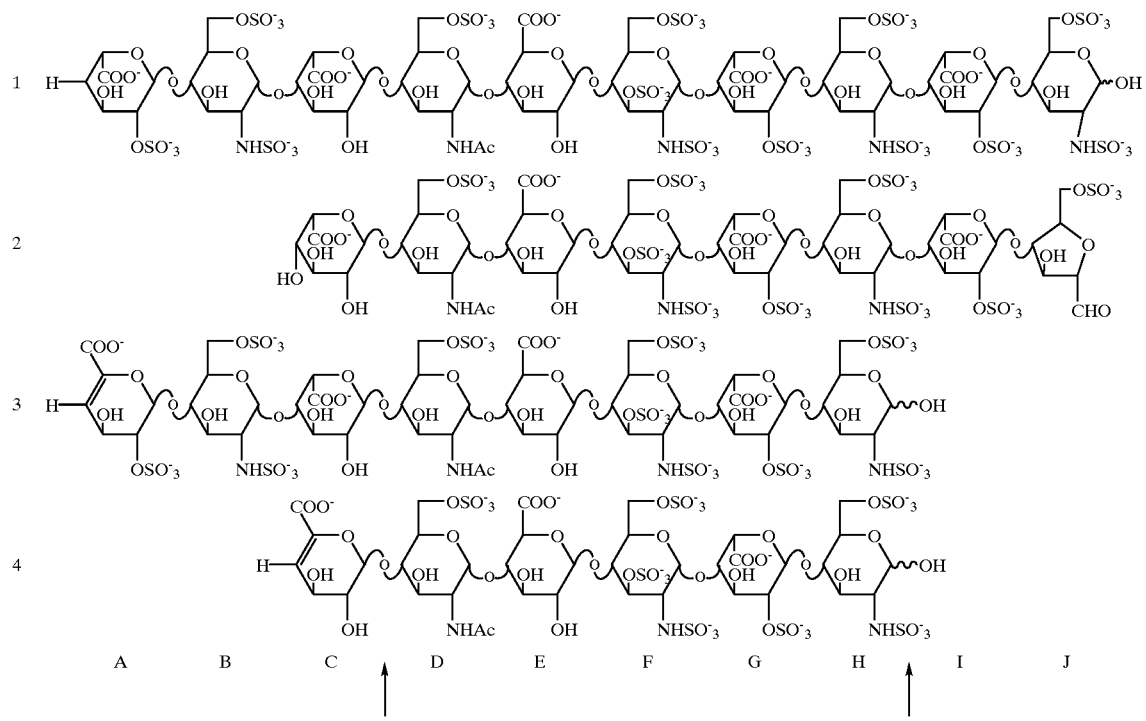

A B C D E F G H I J

The present invention is based upon the discovery that extremely low levels of heparin sulfate marker can be measured using a fluorophore-labeling technique. The technique used in accordance with the present invention is known as FACE®, Fluorophore-Assisted-Carbohydrate-Electrophoresis and involves separating labeled heparins by electrophoresis. Heparin sulfate in a biological sample used for testing may be concentrated or partially degraded with a heparinase and labeled at its reducing ends with a charged or uncharged fluorescent molecule or chromophore. The heparins are also detected by chemiluminescence, antibody-binding assay or spectrophotometric methods.

Fluorophore assisted carbohydrate electrophoresis (FACE®) is described in detail in U.S. Pat. Nos. 4,975,165, 5,035,786, 5,087,337, 5,094,731, 5,094,740, 5,205,917, 5,316,638, 5,340,453, and 5,472,582, the disclosures of which are herein incorporated by reference. Fluorophore-assisted carbohydrate electrophoresis permists the electrophoretic separation of a complex mixture of carbohydraes into distinct bands on a gel. Prior to electrophoresis, a carbohydrate mixture for analysis is treated with a flurorphore label that combines with the reducing end of the carbohydrates for analysis. The fluorophore label permist the quantitative measurement of the labeled carbohydrates by fluorescence. The fluorophore label either is charged or coupled with a charge imparting species when the fluorophore itself is uncharged. Thus the label not only fluorescently tags the carbohydrates, but imparts an ionic charge, permitting hitherto uncharged carbohydrates to migrate in an electric field. Suitable fluorescent labels include by way of example, 8-aminonaphthalene-1;3,6-trisulphonic acid (ANTS), 1-amino-4-naphhthalene sulfonic acid (ANSA), 1-amino-6,8-disulphonic acid (ANDA), lucifer yellow, and 2-aminoacridone.

After the carbohydrates have been labeled, the sample is subsequently subjected to polyacrylamide gel electrophoresis or a similar electrophoresis separation means, in order to separate and concentrate the labeled carbohydrates into bands. The separated carbohydrates may be visualized directly by photoelectric menus fluorescence under U.V. light and the banding patterns stored photographically. Alternatively, the separated carbohydrates may be visualized by photoelectric means, including laser-scanner photomultiplier tube systems and cooled charge coupled devices (CCD). CCDs are semiconductor imaging devices that pemit the sensitive detection of emitted light. CCDs and their uses are described in U.S. Pat. Nos. 4,874,492 and 4,852,137 which are herein incorporated by reference. The image produced by the CCD may be subsequently transferred to a computer wherein the bands may be analyzed with respect to intensity, mobility, standards, and the like.

When performing fluorophore assisted carbohydrate electrophoresis to determine the presence of a carbohydrate of interest such as heparin sulfate, electrophoretic separation should take place to an extent sufficient to independently resolve bands of the carbohydrate of interest. Electrophoresis may proceed past the point where some carbohydrates have been removed from the electrophoresis separation medium. Electrophoresis may be performed in one or in two dimensions.

Fluorophore assisted carbohydrate electrophoresis permits the diagnosis of a variety of diseases that produce alterations in the levels of diagnostic carbohydrates associated with a disease. The present invention is directed to the diagnosis of atherosclerosis by determining the presence of and quantifying heparin sulfate in biological fluids obtained from a mammal. A significant advantage of fluorophore assisted carbohydrate electrophoresis diagnosis is that diseases manifesting themselves through changes in diagnostic carbohydrate levels may be identified without a prior knowledge of the structure of the diagnostic carbohydrate.

In addition to determining the presence of a disease, e.g. atherosclerosis, fluorophore assisted carbohydrate electrophoresis diagnosis may be used to monitor the progression and treatment of the disease, e.g. atherosclerosis. Monitoring the treatment may be performed by observing alterations in the quantities of the diagnostic carbohydrates, e.g. heparin sulfate, observed as treatment progresses. Alterations in diagnostic carbohydrate levels, e.g. heparin sulfate, may be observed by screening for disease in individuals that have not yet displayed adverse symptoms.

Samples for analysis by fluorophore assisted carbohydrate electrophoresis diagnosis may be prepared from many tissues or bodily fluids removed from a subject. Tissues or bodily fluids for analysis necessarily contain at least one carbohydrate, e.g. heparin sulfate, associated with the condition, e.g. atherosclerosis. Suitable tissues or bodily fluids for analysis include blood, urine and the like. Samples may require processing prior to separating and quantifying the diagnostic carbohydrate, e.g. heparin sulfate. The precise method of sample processing may vary in accordance with a number of factors including concentration of diagnostic carbohydrate, e.g. heparin sulfate, concentration of background carbohydrates, presence of interfering molecules, etc. Suitable methods for processing samples include dialysis to remove interfering molecules, ultrafiltration to concentrate the diagnostic carbohydrate, e.g. heparin sulfate, and remove interfering molecules centrifugation to remove interfering particles, precipitation to remove interfering particles and detergent solubilization to release heparins from cells.

The biochemical assay procedures used for the FACE® evaluation of heparin sulfate also lend themselves to other semiautomated or fully automated analytical procedures such as capillary electrophoresis (CE), a methodology which is beginning to replace HPLC in many clinical labs. The separation of carbohydrates using CE has been described in recent publications, such as Honda et al., *Biochem.* 191:228–234 (1990) and Liu et al., *J Chromatography*, 559:223–235 (1991).

It may be advantageous to modify the structure of some heparins by means of cleavage between heparin subunits prior to electrophoretic separation. Suitable methods of cleavage include using acids, bases, and glycosylytic enzymes either endoglycosidases or exoglycosidases. Reasons for treatment of samples include the liberation of linked monosaccharides from glycoconjugates and the generation of heparins that have a more convenient gel migration rate, i.e., better separation from other heparins. Similarly, it may be advantageous to use glycosyl transferases along with donor sugar, if required to produce a more convenient migration rate.

After the diagnostic carbohydrates such as heparin sulfate have been separated by fluorophore assisted carbohydrate electrophoresis, the carbohydrates may be subsequently transferred in situ onto an immobilizing matrix such as a nitrocellulose of nylon membrane by electroblotting or the like. Membranes containing the immobilized diagnostic carbohydrates may be susequently probed with antibodies or similar specific binding reagents so as to indicate the presence and quantity of the carbohydrates of interest.

In a preferred embodiment, the carbohydrate band data from the fluorophore assisted carbohydrate electrophoresis is read by means of a CCD and stored in a computer usable form. The image detected by the CCD or other detection system may be analyzed by image analysis software such as Glyko® FACE® analysis software, Optimas™ or similar image analysis programs. The data may be subjected to analysis by a variety of software programs. Software programs of interest include those with the ability to quantitate band intensity, measure band mobility, determine the relative molecular weight of carbohydrates forming bands, compare the standards with the samples for analysis, remove unwanted background information, and perform various forms of statistical analysis.

In a second aspect, the present invention features methods for assessing risk for and monitoring progression of atherosclerosis by determining the amount of endogenous heparin present in a mammal. In preferred embodiments of the invention, standards may be used to provide a comparison with the heparins in the subject samples; however, the information embodied by the standard, e.g, migration distance, mobility and intensity, may also be obtained from comparison with stored records made from standards previously subjected to analysis under similar conditions. Standards may be labeled prior to labeling the samples for analysis or standards may be labeled at the same time as the standards are labeled for analysis. Furthermore, the heparin in the standards is preferably quantified so as to provide for quantitative or qualitative comparisons with the amount of heparin in the samples for analysis. Individuals having heparin levels that are measured below the normal amounts may be assessed as at an increased risk for atherosclerosis. Risk values may be easily established for patient populations to correlate endogenous heparin levels with the risk for clinical atherosclerotic disease and sequelae resulting therefrom. Such sequelae include for example thrombotic events such as myocardial infarction and stroke. That is, endogenous heparin levels may be correlated to clinical events or clinical manifestations or measurements of atherosclerosis in a known patient group.

In a third aspect, the present invention features methods for treating atherosclerosis and reducing the risk of clinical sequelae resulting from atherosclerosis comprising the step of administering heparin to a mammal. Individuals determined to have low levels of endogenous heparin according to the methods of the present invention may be treated by administering heparin in doses that are effective to prevent atherosclerosis or to inhibit the rate of progression of atherosclerosis. Such dosages may easily and routinely be determined by those skilled in the art. The blood levels of heparin may then be monitored by the FACE® heparin assay described herein to maintain therapeutic blood levels of heparin.

In a fourth aspect, the present invention features a direct assay for monitoring plasma heparin levels. The FACE® heparin assay of the present invention can measure both unfractionated and LMWH and allows measuring the efficacy of present and future anticoagulant treatment programs in a wide variety of conditions. Although newer biochemical methods have been developed using reversed phase high pressure liquid chromatography (HPLC)(Guo et al., *Anal Biochem* 168:54 (1988)), paper chromatography and cationic dye staining (Chen et al., *Clin Chem* 37:832 (1991)), polyacrylamide gel electrophoresis (Oreste et al., *Anal Biochem* 210:136 (1993)), mass spectrometry (Silvestro et al., *Sem Haemost Thromb* 20:281 (1994)), nuclear magnetic resonance (NMR) spectroscopy (Tori et al., *Sem Haemost Thromb* 20:144 (1994)), and electrochemical sensing (Ma et al., *Anal Chem* 65:2078–2084 (1993)), little is known about the biochemical levels of heparin in plasma after administration. Indirect laboratory testing using the activated partial thromboplastin time (aPTT), or the activated clotting time (ACT) is used to monitor and adjust the dose of heparin to maintain anticoagulation in the therapeutic range. Unfortunately, the responsiveness of different aPTT reagents to heparin is inconsistent, and an ideal reagent has yet to be developed (Shojania et al., *Am J Clin Pathol* 89:19 (1988); Van den Besselaar et al., *Thromb Haemost* 63:16 (1990)). Because individuals respond differently to heparin, the relationship between heparin dose and blood level cannot be predicted reliably by surrogate coagulation tests such as the aPTT (Baker et al., *Arch Int Med* 157:2475–2479 (1997); Hyers et al., *Chest* 108(Supp): 335S–351S (1995); Mesters et al, *Blood Coagul Fibrinolysis* 6:665–671 (1995)). In addition, in patients requiring large amounts of heparin for treatment, the aPTT doesn't reflect the amount of heparin required to reach therapeutic levels (Levine et al., *Arch Int Med* 154:49–56 (1994)). The purpose and ultimate goal in treating a patient for a condition such as thromboembolic disease is resolution of the thrombus and restoration of flow without reoccurrence. Functional biologic assays are not reliable, so the total biochemical level of heparin in patients receiving anticoagulant therapy is not being determined, thus creating the possibility that patients may have an excess or deficiency of circulating levels of heparin during therapy. The assay of the present invention can measure both unfractionated and LMWH and allows measuring the efficacy of present and future anticoagulant treatment programs in a wide variety of conditions.

In a fifth aspect, the present invention features kits for assaying for the presence of heparins including heparin sulfate, analyzing biological samples for medical diagnosis, and for the synthesis or manufacture of heparins. Suitable kits enable laboratories to conveniently perform FACE®, FACE® analysis by capillary electrophoresis (FACE-CE), or some other method and may include reagents for performing tests to identify one or more specific results. Such kits may be useful for diagnosing atherosclerosis, assessing risk for developing atherosclerosis in a subject, or assessing severity of atheroslcerosis in a patient. Kits may include standards, fluorescent labels and associated labeling chemicals, heparin specific binding reagents, instructions, sample containers, capillary columns of different construction and coatings or fillings, and polyacrylamide gel reagents and electrophoresis buffers. More complete kits may include equipment for performing FACE-CE, such as liquid handling materials, CE apparatus or components of the same, detectors, lasers, CCDs, computers, software, and the like. Reagents included in FACE-CE kits are preferably provided in premeasured amounts. The kits may also include instructions for performing the FACE-CE method of the present invention.

The invention having been described, the following examples are offered to illustrate the subject invention by way of illustration, not by way of limitation.

EXAMPLE 1

Heparin Sulfate can be Measured Accurately in Human Plasma and Urine

Procedure:

Plasma samples from a patient with atherosclerosis and a normal plasma were obtained. GAGs were precipitated from 500 ul of plasma by adding 0.5 ml of CPC (cetylpyridinium chloride) reagent (0.2M NaCitrate, 0.1% CPC, pH 4.8). The mixture was incubated for 30 minutes at 37° C. The CPC precipitate was recovered by centrifugation for 5 minutes at 14,000×g, and the supernatant was discarded. The CPC pellet was washed by dissolving the pellet in 67 ul 2M LiCl, adding 267 ul of cold ethanol and re-precipitating the CPC for 2 hours at 4° C. The washed CPC pellet was recovered by centrifugation for 5 minutes at 14,000×g and resuspended in 50 ul of $H_2O$. The residue was digested into disaccharides by adding 20 ul of heparinase ABC solution and incubating for 30 minutes at 37° C. The digest was dried in a CVE, and the disaccharides were labeled with a fluorescent tag by resuspending the residue in 5 ul of the fluorophore ANTS (8-aminonapthalene-1,3,6 trisulfonic acid, disodium salt), 0.15M in 15% acetic acid and 5 ul of 1M $NaCNBH_4$ in DMSO. The labeling reaction was completed in 2 hours at 45° C. The vial of labeled oligosaccharides was brought to 200 ul by adding 190 ul of water, and 4 nl was injected into a CE column.

Equipment:

Separation of the fluorescently tagged oligosaccharides was performed on a P/ACE system 5500 capillary electrophoresis apparatus equipped with a diode array detector. Separations were performed on 50 cm long coated capillary columns (Beckman Instruments) using 50 mM Acetate buffer, pH 10.4. Detection was performed by absorption at 214 nm.

Figure 1:
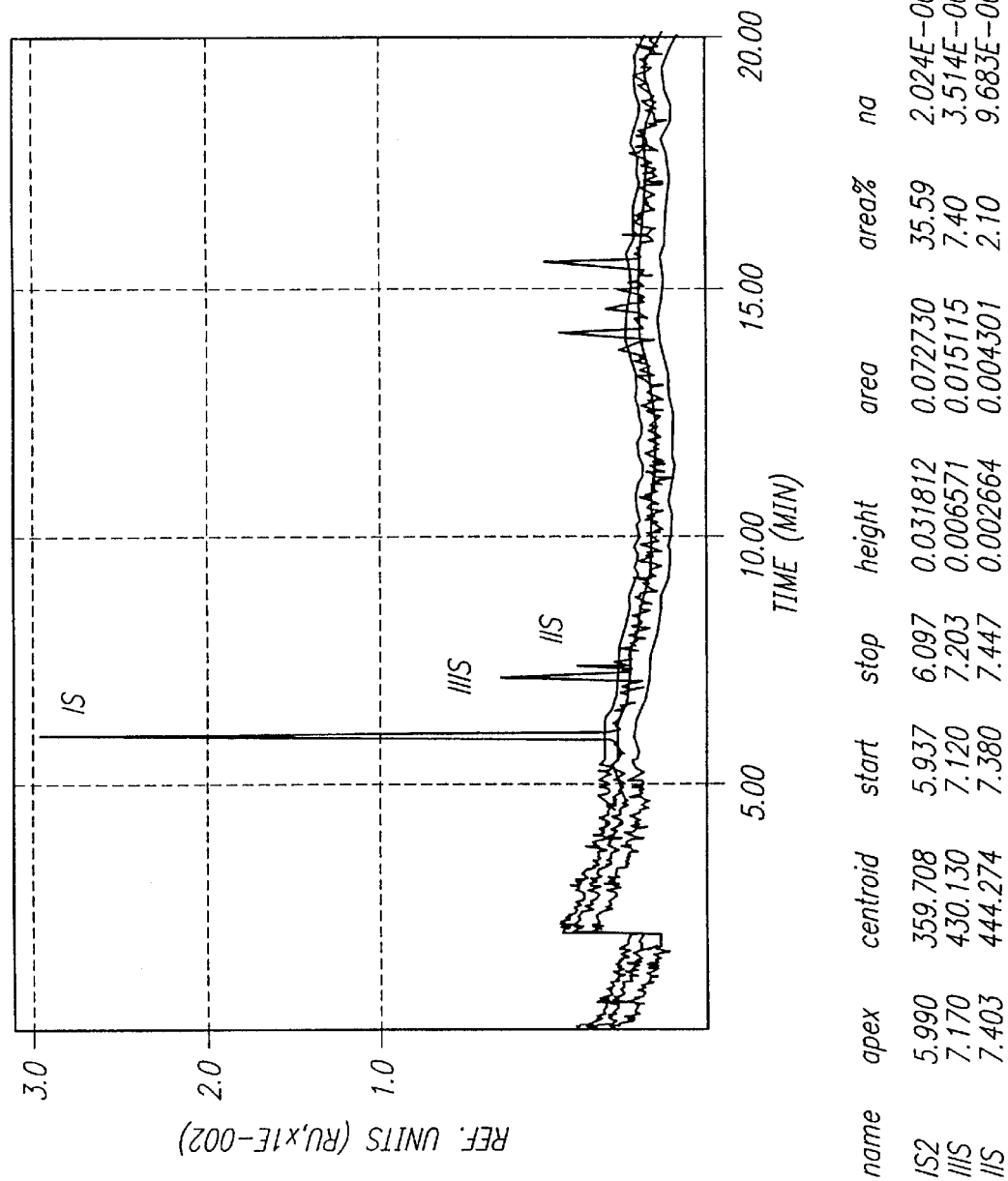
FIG. 1 demonstrates that heparin sulfate may be accurately measured in human plasma and uring using a flurorphore assisted carbohydrate clectrophoresis assay. These data are the results of analysis of 2 mU heparin in 1 cc water. The tracing shows the IS, IIIS and IIS heparin sulfate dissacharides (heparin sulfate DS) obtained from this positive control test. The digitized amount of heparin sulfate DS in each peak can be quantified and the data used to generate the final data. There is a high correlation between the amount of heparin sulfate added to a blank test sample and the amount recovered after assay.

Results of analysis of 2 mU heparin in 1 cc water are shown in FIG. 1. The tracing shows the IS, IIIS and IIS heparin sulfate disaccharides (heparin sulfate DS) obtained from this positive control test. The digitized amount of heparin sulfate DS in each peak can be quantified and the data used to generate the final data. There is a high correlation between the amount of heparin sulfate added to a blank test sample and the amount recovered after assay. In addition, it was demonstrated that the assay for heparin sulfate is linear over at least two orders of magnitude.

EXAMPLE 2

Measurment of Plasma Heparin Sulfate in Normal and Atherosclerotic Patients

Procedure

Plasma samples were collected at various time periods from normal subjects and from patients diagnosed with atherosclerosis by ultrafast CT scan. A plasma sample from a patient with atherosclerosis and a normal plasma was obtained. GAGs were precipitated from 500 ul of plasma by adding 0.5 ml of CPC (cetylpyridinium chloride) reagent (0.2M NaCitrate, 0.1% CPC, pH 4.8). The mixture was incubated for 30 minutes at 37° C. The CPC precipitate was recovered by centrifugation for 5 minutes at 14,000×g, and the supernatant was discarded. The CPC pellet was washed by dissolving the pellet in 67 ul 2 M LiCl, adding 267 ul of cold ethanol and re-precipitating the CPC for 2 hours at 4° C. The washed CPC pellet was recovered by centrifugation for 5 minutes at 14,000×g and resuspended in 50 ul of $H_2O$. The residue was digested into disaccharides by adding 20 ul of heparinase ABC solution and incubating for 30 minutes at 37° C. The digest was dried in a CVE, and the disaccharides were labeled with a fluorescent tag by resuspending the residue in 5 ul of the fluorophore ANTS (8-aminonapthalene-1,3,6 trisulfonic acid, disodium salt), 0.15M in 15% acetic acid and 5 ul of 1M $NaCNBH_4$ in DMSO. The labeling reaction was complete in 2 hours at 45° C. The vial of labeled oligosaccharides was brought to 200 ul by adding 190 ul of water and 4 nl was injected into a CE column.

Equipment

Separation of the fluorescently tagged oligosaccharides was performed on a P/ACE system 5500 capillary electrophoresis apparatus equipped with a diode array detector. Separations were performed on 50 cm long coated capillary columns (Beckman Instruments) using 50 mM Acetate buffer, pH 10.4. Detection was performed by absorption at 214 nm.

Results

Figure 2A:
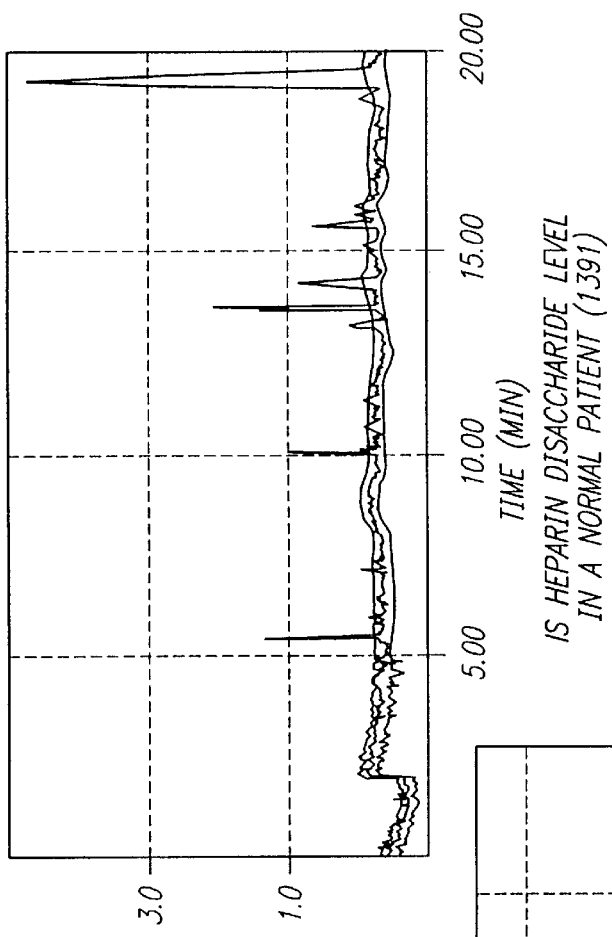
FIG. 2 is an electropherogram of the CE detection of glycosaminoglycan dissaccharides of the plasma from a normal and an atherosclerosis patient. Results are expressed as milliunits of heparin sulfate disaccharide per ml of plasma.
Figure 2B:
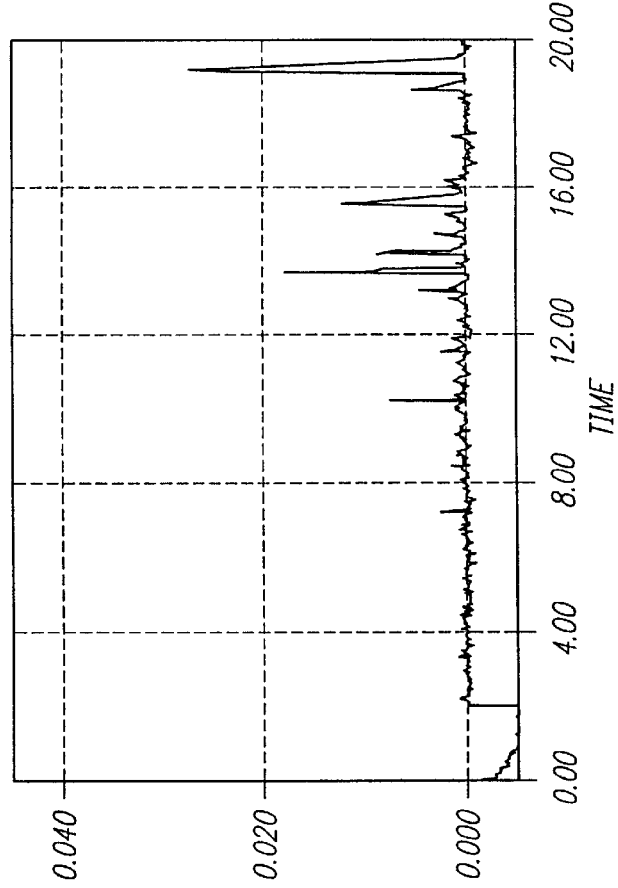

An electropherogram of the CE detection of glycosaminoglycan dissacharides of the plasma from a normal and an atherosclerosis patient is shown in FIG. 2. Results are expressed as milliunits of heparin sulfate disaccharide per ml of plasma.

EXAMPLE 3

Correlation of Plasma Heparin Sulfate and Electron Beam Computed Tomography (EBCT)

Procedure All patients were scanned using the EBCT between Jan. 1, 1993, and Mar. 1, 1996. Patients are part of an ongoing prospective study of heart disease (The Spokane Heart Study). Patients were asked to complete initial and follow-up questionnaires, including a medical history and occurrence of cardiovascular events. Results were analyzed for all consenting, eligible subjects without documented or symptomatic atherosclerotic heart disease.

Electron Beam CT scanning was performed with a Siemens Evolution scanner. Forty contiguous slices 3 mm thick were obtained during a single breath-hold, beginning at the lower edge of the carina. Scan time was 100 ms per slice, with synchronized ECG triggering at 80% of the RR interval. CAC scores were calculated according to Agatston et al., *J Amer Coll Cardiol* 15:827–832 (1990.)

Results

Figure 3:
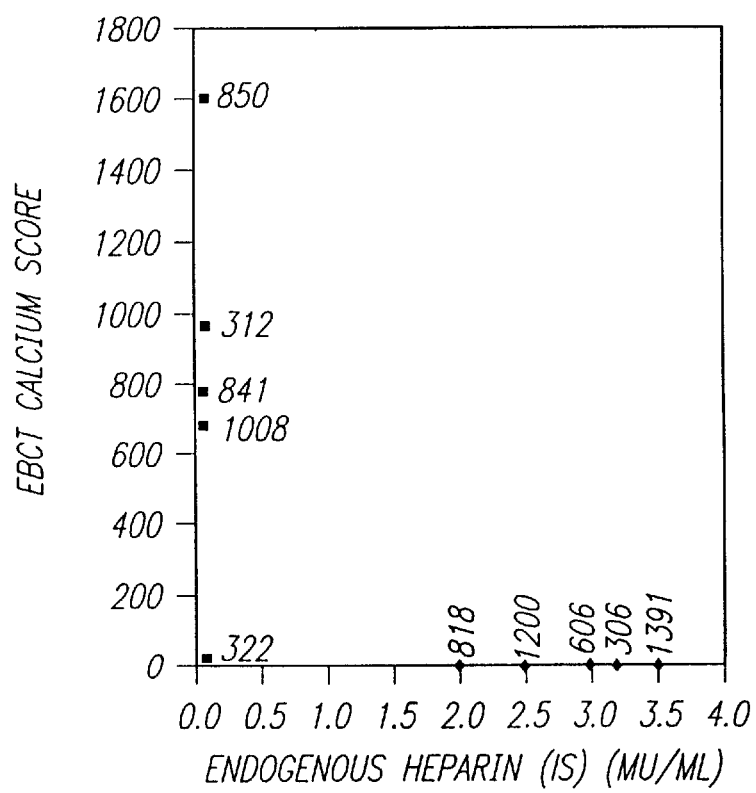
FIG. 3 shows the results of plotting the calcium score against the IS heparin disaccharide level in plasma. Data labels represent individual patient numbers.

FIG. 3 shows the results of plotting the calcium score against the IS heparin disaccharide level in plasma. Data labels represent individual patient numbers. There was greater than 90% correlation between the calcium score and the endogenous heparin level in these patients. One normal patient showed absence of coronary artery calcium and undetectable endogenous heparin.

EXAMPLE 4

FACE Analysis of Heparin Clearance

Flurophore-assisted carbohydrate electrophoresis (FACE®) directly measures the unique biological domains of both unfractionated heparin (UFH) and low molecular weight heparin (LMWH). UFH was measured throughout a wide range of heparin concentrations in plasma. Pharmacokinetic studies in seven studies of normal subjects given 3,000 USP units of UF heparin showed a two-phase compartment model with higher peak plasma levels and shorter elimination times than predicted from previous studies using clotting assays which can overestimate biochemical heparin concentrations. Similarly, FACE® can directly measure LMWH in beagle plasma. The FACE® assay, due to its sensitivity, is also able to measure circulating endogenous production of heparin in both plasma and urine. Heparin is primarily eliminated in the urine in an unchanged form. Direct heparin measurement using the FACE® technique is practical and useful for studies of the correlation of biochemical and biological activities.

To determine the pharmacokinetics and elimination of heparin in humans and to correlate coagulation assay results with total plasma heparin levels, we have developed a convenient and reproducible method for the direct biochemical measurement of heparin. Fluorophore-assisted carbohydrate electrophoresis, FACE®, provides for high resolution separation of sub-picomolar quantities of the glycosaminoglycan heparin in plasma and urine. This technique can be used to measure the predominant biologically active disaccharide in heparin (Lindahl et al., "Biosynthesis of Heparin and Heparan Sulfate in Heparin and Related Polysaccharides", Ofusi and Hirsch eds., New York Academy of Sciences (1998), page 36)). These data report the levels of heparin in normal subjects and compares the results with conventional clotting assays currently used in monitoring patients. Findings demonstrate that unfractionated heparin, given intravenously, has a two-phase elimination process from plasma, and at these doses is largely eliminated by urine excretion. Plasma coagulation assays indicate a longer survival time for heparin than the direct biochemical assay.

Subjects and Methods

Normal human volunteers ranging in age from 23 to 59 years were entered into the study. The study group consisted of four males and one female. These subjects were determined by prior laboratory testing to have a normal coagulation system, were healthy and taking no medications. Body weights varied from 60 to 100 kg. Subjects numbers 1 and 2 underwent repeat testing approximately one month after the initial study and subject number 5 was studied with duplicate samples to evaluate reproducibility, accuracy and precision of the assay system.

Blood samples were drawn, from an indwelling catheter flushed with normal saline into collection tubes with either 3.2% buffer sodium citrate (Becton Dickinson, Rutherford N.J.) or 7.5% EDTA anticoagulant. A bolus of 3,000 units of unfractionated porcine heparin, lot #1 14063, (Elkins-Sinn, Cherry Hill, N.J.) was infused intravenously over three minutes. The catheter was flushed and maintained with a normal saline solution. Blood samples were drawn at baseline, just prior to heparin infusion, and at 10, 20, 30, 45, 60, 120, 180 and 240 minutes. In three of five studies, a five minute sample was obtained. Each blood sample was drawn via a three-way stopcock after the catheter was filled with aspirated venous blood. Urine samples were obtained at baseline, prior to infusion of heparin, and at 30, 60, 90, 120, 180 and 240 minutes in subjects 3, 4 and 5, and at baseline and 60 minutes in subjects 1 and 2 (FIG. 4). Assays for aPTT, prothrombin time (PT), thrombin time (TT), fibrinogen and platelets were performed immediately following collection. Samples for the assay of antithrombin III (ATIII), anti-Xa, tissue factor pathway inhibitor (TFPI) and the FACE® assay of plasma heparin were stored at −70° C. until assayed. Urine samples were frozen at −20° C. for FACE® assay for heparin.

Anticoagulated blood samples were stored on ice and plasma was separated at 4° C. using a double-spin technique. Assays for aPTT, prothrombin time (PT), thrombin time (TT), fibrinogen and ATIII were performed according to standard clinical laboratory procedures. An assay for total TFPI antigen was measured by ELISA (IMUBIND) and anti-Xa by chromogenic substrate (Chromostrate™ Organon Teknica). A complete automated blood cell and platelet count were performed on the EDTA-anticoagulated samples.

LMWH pharmacokinetics were measured in two beagle dogs. The first dog, which weighed 13 kg, received a subcutaneous injection of 50 mg of Enoxaprin® Sodium (Rhone-Poulenc Rorer). The second dog, which weighed 9.4 kg, was given 40 mg subcutaneously. The dose by weight was 3.8 mg/kg in the first dog and 4.2 mg/kg for the second dog. Blood samples were drawn into 3.2% buffer sodium citrate at baseline, 10, 20, 30, 45, 60, 75, 90, 105, 120, 240, 360, 600, and 1440 minutes post-injection. Samples were handled and assays run in a manner similar to the studies of unfractionated heparin in humans.

The 1 S disaccharide fraction of heparin (($\alpha\Delta$Uronic acid-2-$SO_4$(1–4)N-acetylglucosamine-$NSO_4$-$6SO_4$) in plasma and urine was measured using FACE® (28).

Samples were thawed at 37° C. for 20 minutes. For plasma, a 100 μl sample was extracted with 100 μl chloroform. The aqueous phase was adjusted to 2.0 M ammonium acetate and three volumes of ethanol were added. Following a 30 minute incubation on ice, the precipitate was recovered by centrifugation at 14,000 g for 10 minutes. For urine, a 500 μl sample was precipitated with an equal volume of 1% CPC reagent. Pellets for both were dried in a centrifugal vacuum evaporator (CVE). Five μl heparinase 1 (Glyko, Novato, Calif.) was added, and the sample was incubated for one hour at 37° C. The digest was dried in a CVE and resuspended in 5 pl of the fluorophore 8-aminonaphthalene-1,3,6 trisulfonic acid (ANTS) 0.15 M in 15% acetic acid with 5 μl 1M NACNBH, in DMSO. The mixture was incubated for 16 hours at 37° C. Samples were dried and resuspended in 10 μl water. Two microliters of the resuspended material were combined with 2 μl 30% glycerol. The entire 4 μl was loaded onto a single lane of a precast 35% polyacrylamide slab gel (Glyko, Novato, Calif.) and run at 15mA constant current for 1–2 hours at 20° C.

Imaging of the gels was performed on the FACE® imaging system (Glyko, Novato Calif.) with individual bands quantitated using the software supplied with the imager. Standard curves for heparin were generated and standard disaccharides were used to quantitate the amount of trisulfated disaccharide common to heparin found in the sample. Results were obtained as picomoles of heparin disaccharide per ml and converted to Units of heparin per ml (U/ml), using a standard curve of heparin in plasma or urine.

Results

The FACE® assay for reducing sugars is widely used for quantitation of oligosaccharides derived from glycoproteins, glycolipids, and proteoglycans (Starr et al., *J Chromatography* 720:295–321 (1996)) and has applications in multiple diseases (Klock et al., "The Different Faces of Disease: FACE® diagnosis of disease", Glycoimmunology, Alave and Axford eds., (1995), pages 13–25). Results of the assay for bovine lung heparin are shown in FIG. 5. For heparin disaccharide analysis, the method was validated using various heparin pharmaceutical standards. A dose-response study of the 1 S fraction of heparin is shown in FIG. 6. In this assay, the number of U/ml of heparin in subject plasma at each time point was determined using the amount of heparin disaccharide recovered from normal plasma spiked with increasing amounts of bovine lung heparin (Upjohn). The dose-response of 1S disaccharide was linear within the therapeutic range of heparin. The amount of heparin in subject plasma was determined at each time point by extrapolation from the dose-response plot. For example, a plasma sample containing 17 pmoles of the 1S disaccharide, as measured by FACE®, contains 0.15 U/ml plasma heparin. The assay sensitivity is 0.025 U/ml plasma, precision is 5.1% CV (n=16), and recovery from plasma is >80%.

The reproducibility of the assay was determined in subject 5 where duplicate samples were taken over the first 45 minutes. Samples were prepared and individually assayed with excellent reproducibility (r=0.998), as shown in Table 1.

The pharmacokinetics of heparin clearance were determined in seven subject studies (five subjects and two repeat studies of subjects 1 and 2) following a 3,000 unit IV bolus of porcine heparin (FIG. 7). Mean plasma heparin levels reached a peak within five minutes after the infusion of heparin. Peak heparin levels ranged from 0.16 to 1.45 U/ml. At 60 minutes, the average plasma heparin level was 0.166 U/ml. Levels then fell. The time for the concentration of heparin dropping by one half of the original peak concentration was approximately 10 minutes. This represents the alpha-phase which is driven primarily by the distribution of heparin from plasma into the tissue. The slope of the beta-phase governed primarily by elimination of heparin from the plasma yielded a mean half-life ($T_{1/2}$) of approximately 45 minutes. Heparin levels were undetectable by three hours.

The plasma level of heparin appears to be inversely related to the body weight of the subject. The subject with the level of 0.16 U/ml weighed 100 kg while the subject with the level of 1.45 U/ml weighed 56.8 kg. This relationship held for six of the seven subjects. The importance of the relationship between body weight and heparin-induced anticoagulation of a person is shown in FIGS. 8 and 9. The seven subjects were separated into two groups. The first group (FIG. 8) weighed between 81.8 and 104.5 kg (five studies, 3 subjects) and the second group (FIG. 9) weighed between 56.8 and 61.4 kg (two studies, 2 subjects). The amount of circulating heparin necessary for therapeutic anticoagulation is believed to be 0.2 to 0.4 U/ml. This can be referred to as the "therapeutic window." In the higher weight group (FIG. 8), mean heparin levels fell within the therapeutic window for only the first 35 minutes, while the mean aPTT stayed within the therapeutic window for approximately 60 minutes. In the low weight group, FACE® heparin levels remained in the therapeutic range for approximately 40 minutes while the aPTT remained for about 105 minutes. Both assays reached baseline values by 240 minutes.

When FACE® plasma heparin levels were compared to the aPTT (FIG. 10), a therapeutic window ranging from 0.2 to 0.4 U/ml was used. Using the FACE® assay which directly measures the heparin molecule, we found heparin levels dropping below 0.2 U/ml by approximately 35 minutes, while the corresponding aPTT level remained within the therapeutic window of 0.36 U/ml. The aPPT did not fall below the 0.2 level until approximately 68 minutes. Both assays reached baseline by three hours. We then compared the levels of anti Xa activity to the direct FACE® assay (FIG. 11). The anti-Xa activity and FACE®® heparin levels initially rose to levels above the therapeutic range. FACE® plasma heparin levels dropped below the 0.2 U/ml level at about 30 minutes and the anti-Xa activity at around 70 minutes.

Plasma TFPI antigen rose rapidly with a mean $T_{1/2}$ of approximately 70 minutes with first order decay to baseline by 180 min. The infusion of heparin resulted in a large release of TFPI (4× baseline) (FIG. 12).

Simultaneous assays of urine for heparin revealed surprising levels. When urine samples were labeled directly with ANTS without using extraction or heparinase, intact heparin chains were detected (data not shown). Disaccharide and monosaccharide profile analysis also confirmed that the heparin in urine was chemically identical to plasma heparin (data not shown). Kinetics of the appearance of heparin in urine is shown in FIG. 13. Quantitative recovery demonstrated that over 80% of the amount of heparin injected was recovered in the urine over a 4-hour period. Also of note was the observation that heparin levels could be detected in the urine prior to the administration of heparin in six of the seven subjects with a mean level of 0.18 U/ml. The only subject for which baseline heparin levels were not detected was the single female subject.

Baseline, preinjection plasma levels of heparin were detected in two of the seven studies. Results were from two different male subjects with a mean level of 0.045 U/ml. This observation most likely represents endogenous production of heparin by subjects since none had previously been exposed to exogenous heparin. The mean aPTT was 27.1 seconds in the group where baseline levels of plasma heparin were absent, and 29.2 seconds where plasma levels were detected.

Simultaneous blood count and coagulation parameters were determined in the study subjects. There were no significant changes in the hemoglobin or white blood count. Similarly, the platelet count, fibrinogen and ATIII levels were normal throughout, but the prothrombin time was mildly influenced over the first 90 minutes with peak influence occurring at five minutes. (Table 2). The aPTT failed to show good correlation with the plasma heparin levels and returned to baseline well after the normalization of plasma heparin levels in all subjects (FIG. 7).

The measurement of LMWH (Enoxaparin) in beagle dogs is shown in FIG. 14. The curve represents the mean FACE® measurements of two dogs which received a mean of 4 mg per kg of body weight subcutaneously. The FACE® disaccharide was measured at baseline and at 13 time points over the next 24 hours. Heparin levels peaked at 45 minutes and exponentially fell to baseline after 1440 minutes. The $T_{1/2}$ was approximately 135 minutes. As in humans, a basal plasma endogenous level of heparin was detected.

Discussion

The current study uses the FACE® dissacharide assay as a direct biochemical measurement of biologically active heparin. The predominant disaccharide in heparin is measured and quantitated using known standard structures. In the range required for clinical monitoring of patients receiving heparin, the dose-response of the assay is linear. Confidence in this assay is based on work of more than 1000 animal and human clinical studies, plus work of others analyzing glycosaminoglycan disaccharides (Klock et al., "Pharmacokinetics by direct biochemical measurement of heparin and low molecular weight heparin using FACE", First Internet Glycotechnology Conference (September, 1995), In press). The use of a heparinase enzyme which is specific for the N-sulfated site in the heparin disaccharide, and the specific separation of the digested disaccharides makes this assay a reliable means for assessing the presence of heparin in plasma and urine.

Most studies of the pharmacokinetics of heparin in humans have relied directly or indirectly on a biological (clotting) assay or have depended upon ion exchange chromatography and/or cationic dye staining which may not be specific for heparin. When clotting assays are used to follow a heparin dose in normal subjects (Kayser, "Heparin: Mechanism of Action", Textbook of Therapeutics: Drug and Disease management, Herfindal and Gourley eds., (1996), p. 861); Hirsch, Circulation 89:1449–1468 (1994)), kinetics are exponential with an initial rapid clearance, followed by a second longer elimination time. In both instances, based on the biological assay, the half-life increases with the dosage of heparin (Nyman et al., Thromb Diath Haemorrh 33:102–104 (1974)). These results most likely represent a combination of a saturable and first-order mechanism for the disappearance of heparin. The current studies support this model with an initial phase of rapid elimination representing distribution, and the second phase representing a non-linear removal of heparin from the circulation (FIG. 7). There have been many studies to explain the elimination of heparin. One study reported that heparin is removed from the circulation in an intact, free form, not bound to ATIII (Bjornsson et al, Clin Parmacol Ther 31:104–113 (1982)). Others have postulated that endothelial and reticuloendothelial cells of the liver are primarily responsible for the degradation and removal of heparin (Cuestermans et al., J Biol Chem 257:3401 (1982); Jaques, Science 206:528 (1979)). Still others have noted the presence of heparin metabolic products in the urine (McAvoy, Clin Pharmacol Thera 25:372 (1979)). Our findings provide new information which may explain the elimination of heparin from the circulation. The rapid appearance of relatively intact heparin in urine (discussed later) following an intravenous bolus suggests a renal tubular transport mechanism. Single-dose elimination studies would need to be supplemented with continuous-infusion studies to confirm this.

The half-life of the anticoagulant effect of heparin has been reported by others to be approximately 90 minutes (Greenberg et al., Clinical Pharmacology Basic Principles in Therapeutics, Melmon et al., eds. (1992), pages 558–563; Wessler et al., Blood 53:525–544 (1979); deSwart et al., Blood 60:1251–1258 (1982)). As the dose of heparin increases, so does the half-life of circulating heparin (Nyman et al, supra), while the opposite occurs in the presence of extensive thrombosis such as a massive pulmonary embolism (Hirsch et al., Circulation 53:691–696 (1976)). This variable anticoagulant response in acute disease processes most likely reflects the binding of heparin to plasma proteins (Mason et al., J Lab Clin Med 130(6):649–655 (1997)). In both instances, dosage adjustment is critical to patient outcome. The direct measurement of heparin using the FACE® assay shows the half-life to be shorter than previously reported. Within a 10 minute period, half of the circulating heparin had been removed from the circulation (FIG. 7). This occurs during the distribution phase. The second or elimination phase half-life is about 45 minutes, with the heparin being easily measured in the urine.

These data demonstrate discrepancies between the clotting based and biochemical assay-based heparin levels in all the subjects. For the heparin doses given, the clotting studies typically overestimate the biochemical amount of heparin in the circulation. When the aPTT was compared to the FACE® heparin measurement (FIG. 10), a disparity was seen after the initial peak of five minutes. Using a therapeutic window of 0.2 U/ml to 0.4 U/ml of heparin and a corresponding aPTT range between 40 to 80 seconds (1½ to 3 times baseline), we found that plasma heparin concentrations fell below the window after 30 minutes. However, the aPTT remained well within the therapeutic window and did not fall outside until after 60 minutes. A similar finding was found when the anti-Xa assay was compared to the FACE® heparin assay (FIG. 11). Others have observed discrepancies between assays for heparin in normal human subjects given similar doses of heparin. In one study, the aPTT and the anti-Xa assays were disparate with the anti-Xa assay giving higher numbers than the aPTT (Bjornsson et al, supra). In another study (deSwart et al., Thromb Haemost 52:6 (1982)), the aPTT assay gave a higher result than a hexadimethrine bromide neutralization assay with the thrombin time as an end point. These results point out some of the problems with the biological assays of heparin.

Levels of TFPI were dramatically increased by the infusion of heparin. TFPI is important as an inhibitor of the initial stages of coagulation activation. TFPI is a direct inhibitor of factor Xa. The complex inhibits the extrinsic system by inhibition of the VII-a Tissue Factor complex (Rapaport, Thromb Haemost 66:6–15 (1991); Rapaport et al, Thromb Haemost 74:7–17 (1995)). Levels of TFPI disappeared from the circulation in a manner similar to heparin and anti-Xa by dropping below baseline values by 180 minutes (FIG. 12). The major difference between the direct heparin assay and the anti-Xa level is that anti-Xa levels remain elevated much longer. This elevation suggests that the heparin is present in the therapeutic range when, in fact, direct measurement of heparin fails to support this. Perhaps this observation can be explained by the influence of TFPI which may also explain discrepancies between heparin disaccharide and the aPTT which remains prolonged after heparin is cleared. TFPI released by heparin has been shown to prolong the aPTT as will the addition of TFPI alone to plasma (Lindahl et al., *Thromb Res* 62:607–614 (1991)). TFPI is a direct inhibitor of Xa and will prolong the anti-Xa assay (Broze et al., *Biochemistry* 29:7539–7546 (1990)) As the concentration of heparin is increased, there is a corresponding linear prolongation of the aPPT (Kristensen et al., *Throm Haemost* 68(3):310–314 (1992)). As the concentration of heparin is reduced during the process of elimination, the concentration of TFPI remains in the therapeutic range for a longer period as is reflected by the coagulation assays.

After injection of a modest dose of heparin, a rapid appearance of largely intact heparin in the urine was observed. This is consistent with studies in dogs which showed that after large intravenous doses of heparin, intact (active as anticoagulants) heparin was found in the urine (Hirsch et al., supra). By measuring sulfated heparin disaccharides by monosaccharide analysis and by characterizing heparin directly without enzymolysis (data not shown), this study has concluded that the heparin which appears in the urine of these subjects is still highly sulfated, of high molecular weight, and chemically identical to the injected material. Although peak concentrations of heparin in the urine were observed at 30 minutes, they may have occurred earlier than the initial 30-minute sampling time.

Significant amounts of heparin were present in baseline samples of urine in 6 of the 7 subjects. Since none of these subjects had previously been exposed to exogenous heparin, this most likely represents the excretion of endogenous heparin. In general, endogenous heparin has not been appreciated, even though it's presence has been suspected for some time since mast cells contain active heparin (Metcalfe, "Mastocytosis", *Cecil Textbook of Medicine*, 18th ed., Smith et al, eds. (1988), page 1483). Endogenous heparin has not been identified except in extreme conditions such as systemic mastocytosis where heparin is indirectly measured by a slight prolongation of the aPTT (Majerus et al, *The Parmacological Basis of Therapeutics*, 9th ed., Hardman et al, eds., (1996) pages 1343–1335).

The significance of endogenous heparin is unclear but may play a role in the modulation of the hemostatic process, especially through the inactivation or inhibition of factors responsible for the integrity of the system. Engelberg and co-workers (Engelberg, *Clin Appl Thromb Haemost* 2:83 (1996)) were able to measure endogenous heparin and later showed that endogenous heparin levels were inversely related to cholesterol and lipoprotein levels (Engelberg, *Circulation* 23:573–577 (1961)). A deficiency may therefore be a major factor in the pathogenesis of atherosclerosis (Engelberg, *Semin Thromb Haemost* 14:88–105 (1988)). Recently, it has been shown that reduced lipoprotein lipase (LPL) activity results in lower levels of high density lipoproteins with the resultant—increased susceptibility to coronary artery atherosclerosis (Durrington, *Lancet* 342:1315–1316 (1993)). If heparin is not available for LPL binding, loss of function results with elevation of low density lipoproteins (Berg et al., *Proc Natl Acad Sci USA* 87:347–348 (1990)). The implication of this observation and the relationship to atherosclerosis needs to be studied further.

The measurement of heparin in plasma and urine has direct consequences for the adjustment of heparin dosage in patients with an existing thrombosis. The importance of the renal clearance of heparin has been known for some time (Cadroy et al., *Thromb Res* 63:385 (1991)), with individual patient reaction varying widely. Thus, the optimal dose for any given patient must be determined by trial and error. The development of consistent and reliable biochemical assays for heparin and its subcomponents may contribute to a better understanding of the role of clotting-based assays in patient management, and possibly in the development of more efficient methods for determining the dose of heparin in a patient. In addition, with the direct measurement of heparin, the agonizing problems of the standardization of manufactured heparin products may be eliminated as well as the problems of removing plasma from cells, plasma to citrate anticoagulant and the timely freezing of the sample.

The biochemical measurement of heparin in plasma and urine is a practical method which can be used for the quantitative analysis of unique biochemical domains in heparin which can, in turn, be a useful tool for studies of the correlation of biochemical and biological activities. The increased sensitivity of the FACE® heparin assay now makes it possible to measure endogenous production of heparin in the blood and urine (Cavari et al., *Thromb Res* 67:157–165 (1992)). This assay, which can measure both unfractionated and LMWH, allows measuring the efficacy of present and future anticoagulant treatment programs in a wide variety of conditions. The assay can be modified to measure the heparin disaccharide in whole blood. This is important in vivo, since whole blood, not plasma alone, clots to form the basis of the thrombus. The speed of the assay will be greatly enhanced along with the development of specific hardware to provide patient "point of care" support.

Although the invention has been described with reference to the presently preferred embodiments, it should be understood that various modifications can be made without departing from the spirit of the invention. Accordingly, the invention is limited only by the following claims.

TABLE 1

Reproducibility of FACE ® Heparin measurement in subject #5.
Duplicate samples obtained over the first 45 minutes following intravenous injection of 3,000 units UFH (r = .998).

| Time from Injection | FACE ® Heparin (U/ml) | |
|---|---|---|
| | Subject 5 | Subject 5 Repeat |
| Baseline | 0 | 0 |
| 5 min | 1.45 | 1.28 |
| 10 min | 0.75 | 0.73 |
| 20 min | 0.78 | 0.70 |
| 30 min | 0.74 | 0.68 |
| 45 min | 0.60 | 0.54 |

TABLE 2

Mean values for the PT, ATIII, fibrinogen and platelet count over time in subjects following intravenous injection of 3,000 units unfractionated heparin IV.

| Time from Injection | Mean PT (sec) | Mean AT3 (% Activity) | Mean Fibrinogen (mg %) | Mean Platelets (x10$^3$) |
|---|---|---|---|---|
| BASE | 11.2 | 288 | 292 | 178 |
| 5 min | 14.0 | 281 | 288 | 185 |
| 10 min | 13.6 | 290 | 291 | 177 |
| 20 min | 13.1 | 281 | 281 | 179 |
| 30 min | 12.5 | 283 | 274 | 181 |

TABLE 2-continued

Mean values for the PT, ATIII, fibrinogen and platelet count over time in subjects following intravenous injection of 3,000 units unfractionated heparin IV.

| Time from Injection | Mean PT (sec) | Mean AT3 (% Activity) | Mean Fibrinogen (mg %) | Mean Platelets (x10$^3$) |
|---|---|---|---|---|
| 45 min | 12.4 | 283 | 283 | 182 |
| 60 min | 12.1 | 274 | 274 | 183 |
| 90 min | 11.7 | 289 | 290 | 178 |
| 120 min | 11.6 | 281 | 281 | 182 |
| 180 min | 11.3 | 279 | 279 | 179 |
| 240 min | 11.3 | 273 | 273 | 178 |

What is claimed:

1. A method for treating atherosclerosis and reducing the risk of clinical sequelae resulting from atherosclerosis comprising the steps of:
   (a) identifying subjects having atherosclerosis or at increased risk for developing atherosclerosis using fluorophore assisted carbohydrate electrophoresis to determine the amount of endogenous heparin present in the subject; and
   (b) administering a therapeutically effective dose of heparin to the subject.

2. The method of claim 1, wherein said endogenous heparin is determined using fluorophore assisted carbohydrate comprising the steps of:
   (a) obtaining a biological sample;
   (b) reacting the carbohydrates in said sample with a moiety capable of fluorescing in order to form a conjugate of the carbohydrate and the moiety capable of fluorescing;
   (c) subjecting the conjugate to electrophoretic separation in a gel;
   (d) electro-blotting the separated saccharides in the gel to the surface of a support membrane; and
   (e) contacting labeled probes with the membrane and determining binding affinity of the probes to the conjugate.

3. The method according to claim 2, wherein the fluorescence assisted carbohydrate electrophoresis is performed using a fluorophore selected from the group consisting of 8-aminonapthalene-1,3,6-trisulphonic acid (ANTS), 1-amino-6,8-disulphonic acid (ANDA), 1-amino-4-napthalene sulfonic acid (ANSA), lucifer yellow and 2-aminoacridone (AMAC).

4. The method according to claim 2 further comprising the step following (a), of modifying a heparin sulfate in the biological sample with a heparinase.

5. The method according to claim 2 further comprising the step following (a), of adding a chromophore to the biological sample.

6. A method according to claim 2 further comprising the step before (c), of adding an enzyme to the biological sample that chemically alters heparin sulfate or removes a fluorescent tag from a heparin.

7. The method according to claim 2 further comprising the step following (a), of modifying the heparin to make the heparin more susceptible to fluorophore labeling.

8. The method of claim 1, wherein said amount of endogenous heparin is determined in the plasma.

9. A method for treating atherosclerosis and reducing the risk of clinical sequelae resulting from atherosclerosis comprising the steps of:
   (a) obtaining a biological sample;
   (b) separating heparin sulfate from other carbohydrates that may be present in the sample by fluorophore assisted carbohydrate electrophoresis;
   (c) comparing the quantity of heparin sulfate present in the sample with the quantity of heparin sulfate present in a reference standard wherein the reference standard is from a patient know to have significant atherosclerosis or known to be without significant atherosclerosis to determine the risk for atherosclerosis; and
   (d) administering a therapeutically effective dose of heparin to the subject.

10. The method according to claim 9, wherein heparin sulfate is a component of a glycoconjugate.

11. The method according to claim 9, further comprising the step following (a), of adding a purified heparin sulfate-modifying enzyme and a fluorophore labeled heparin standard to the biological sample.

12. The method according to claim 9, further comprising the step following (e), of quantifying the amount of heparin sulfate using a UV absorbance measuring fixed or variable wavelength type detector.

13. The method according to claim 9, further comprising the step following (e), of quantifying the amount of heparin sulfate using a laser or noncoherent light source induced fluorescence and either a variable or fixed wavelength detector.

14. The method according to claim 13, wherein the measurements from said detector are stored and analyzed by a computer program.

* * * * *